United States Patent
Nelson et al.

(10) Patent No.: US 6,479,286 B1
(45) Date of Patent: Nov. 12, 2002

(54) METHODS AND COMPOSITIONS FOR MAKING DENDRITIC CELLS FROM EXPANDED POPULATIONS OF MONOCYTES AND FOR ACTIVATING T CELLS

(75) Inventors: Edward L. Nelson, Eldersburg; Susan L Strobl, Hagerstown, both of MD (US)

(73) Assignee: The United States of America as represented by the Secretary of the Department of Health and Human Services, Washington, DC (US)

(*) Notice: Subject to any disclaimer, the term of this patent is extended or adjusted under 35 U.S.C. 154(b) by 0 days.

(21) Appl. No.: 09/424,173
(22) PCT Filed: May 20, 1999
(86) PCT No.: PCT/US98/10311
§ 371 (c)(1), (2), (4) Date: Jun. 5, 2000
(87) PCT Pub. No.: WO98/53048
PCT Pub. Date: Nov. 26, 1999

Related U.S. Application Data

(60) Provisional application No. 60/047,348, filed on May 21, 1997.

(51) Int. Cl.[7] ............... C12N 5/00; C12N 15/63; A61K 35/00
(52) U.S. Cl. ............... 435/377; 435/325; 435/375; 435/455; 424/93.1; 424/93.4; 424/93.71
(58) Field of Search ............... 435/325, 375, 435/377, 455; 514/44; 424/93.21, 93.71

(56) References Cited

U.S. PATENT DOCUMENTS

| 5,994,126 A | * | 11/1999 | Steinman | 435/325 |
| 6,017,527 A | * | 1/2000 | Maraskovsky et al. | 424/93.71 |

FOREIGN PATENT DOCUMENTS

| WO | WO 94 02156 A | 2/1994 | C12N/5/08 |
| WO | WO 95 34638 A | 12/1995 | C12N/5/08 |
| WO | WO 96 23060 A | 8/1996 | C12N/5/08 |

OTHER PUBLICATIONS

Bossart, et al., "Virus–mediated delivery of antigenic epitopes into dendritic cells as a means to induce CTL," *J. Immunology*, 158(7):3270–3276 Apr. 1, 1997.

(List continued on next page.)

*Primary Examiner*—James Ketter
*Assistant Examiner*—Q Janice Li
(74) *Attorney, Agent, or Firm*—Townsend and Townsend and Crew LLP

(57) ABSTRACT

Methods of generating IL-3 expanded populations of monocytes and differentiating the cells into dendritic cells are provided. The methods include use of the dendritic cells to activate T-cells, in vitro and in vivo, and for ex vivo and other therapeutic methods.

53 Claims, 13 Drawing Sheets

OTHER PUBLICATIONS

Reeves, et al., "Retroviral transduction of human dendritic cells with a tumor–associated antigen gene," *Cancer Research*, 56:5672–5677 (Dec. 15, 1996).

Strobl, et al., "Evaluation of cytokine and chemokine expression in human peripheral blood monocyte derived type I and type II dendritic cells," *Cytokine*, 9(11):938 Abstract No. 194 (11/97).

Tsai, et al., "Identification of subdominant CTL epitopes of the GP100 melanoma–associated tumor antigen by primary in vitro immunization with peptide–pulsed dendritic cells," *J. Immunology*, 158(4):1796–1802 (Feb. 15, 1997).

Zhou, et al., "CD14+ blood momocytes can differentiate into functionally mature CD83+ dendritic cells," *Proc. Natl. Acad. Sci. USA*, 93:2588–2592 (Mar. 1996).

Caux et al. Blood Mar. 1996; 15:87:2376–85.*

Kawakami et al. Int Rev Immunol Feb. 1997;14:173–92.*

Pickl et al. J Immunol Nov. 1996;157:3850–9.*

Encyclopedia Britannica Online.*

HW Snoeck et al., Leukemia, "Interleukin 4 and interferon costimulate the expansion of early human myeloid colony–forming cells. Proposal of a model for the regulation of myelopoiesis by interleukin 4...immune response," 1996, 10, 117–122.*

B Wormann et al., Leukemia, "Proliferative effect of inter-leukin–3 on normal and leukemic human B cell precursors," Abstract, Jun. 1989, 3(6):399–404.*

* cited by examiner

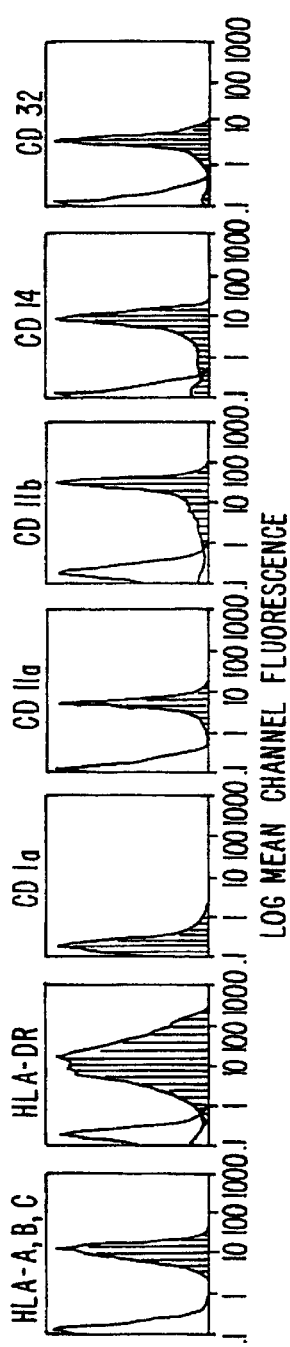
FIG. 5A. MONOCYTES
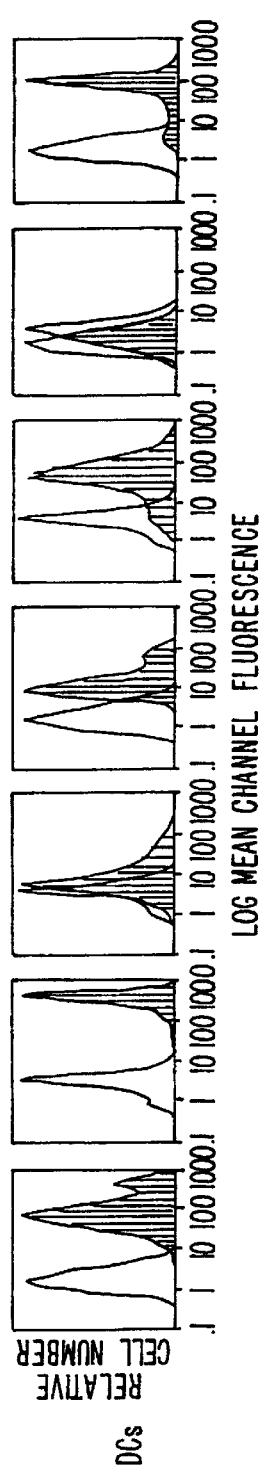
FIG. 5B. BASELINE DCs
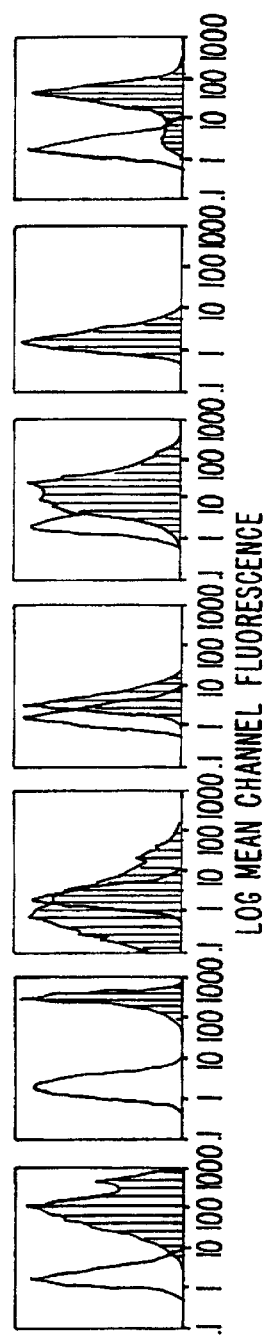
FIG. 5C. TNF-α ACTIVATED DCs

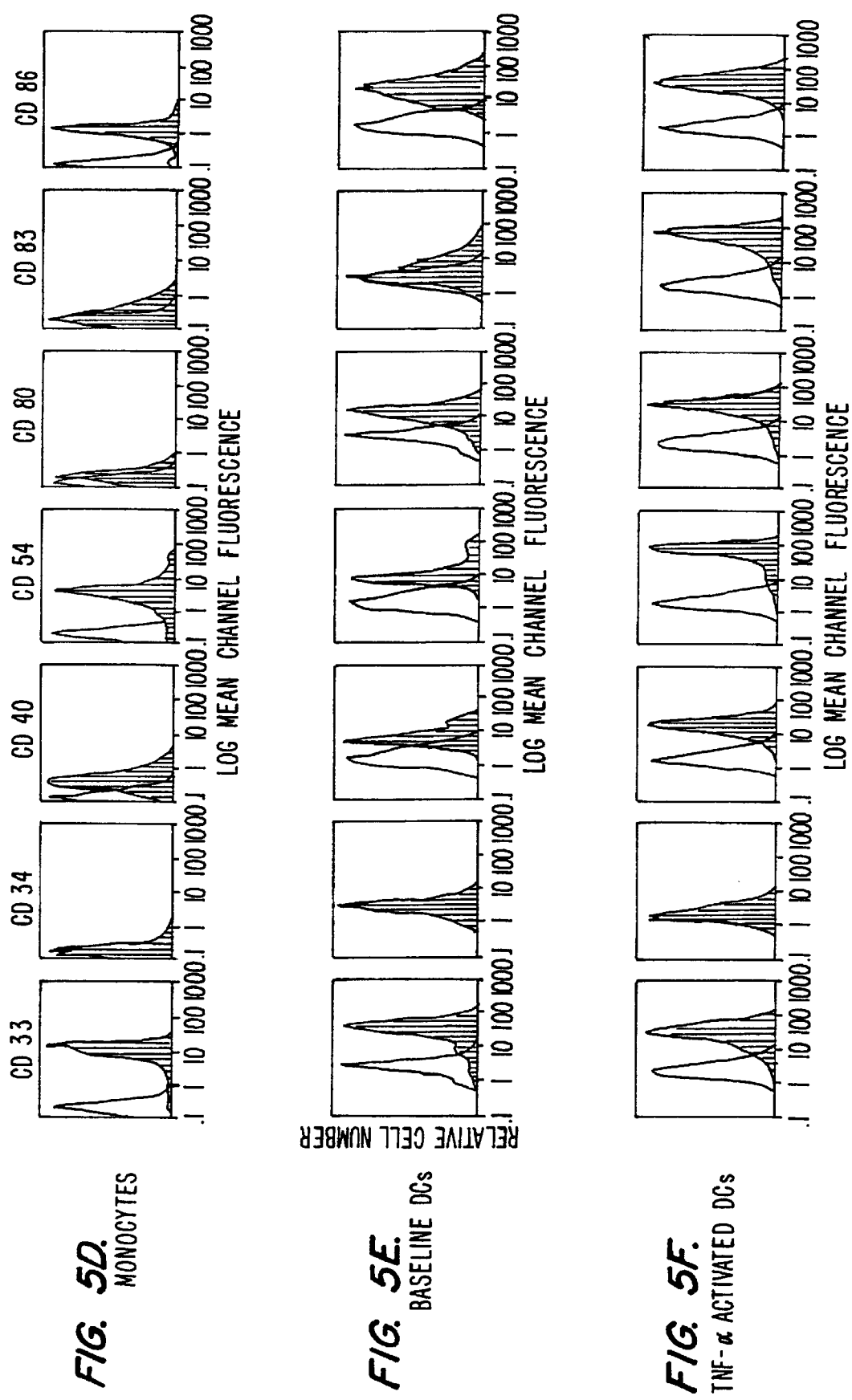
FIG. 5D. MONOCYTES
FIG. 5E. BASELINE DCs
FIG. 5F. TNF-α ACTIVATED DCs

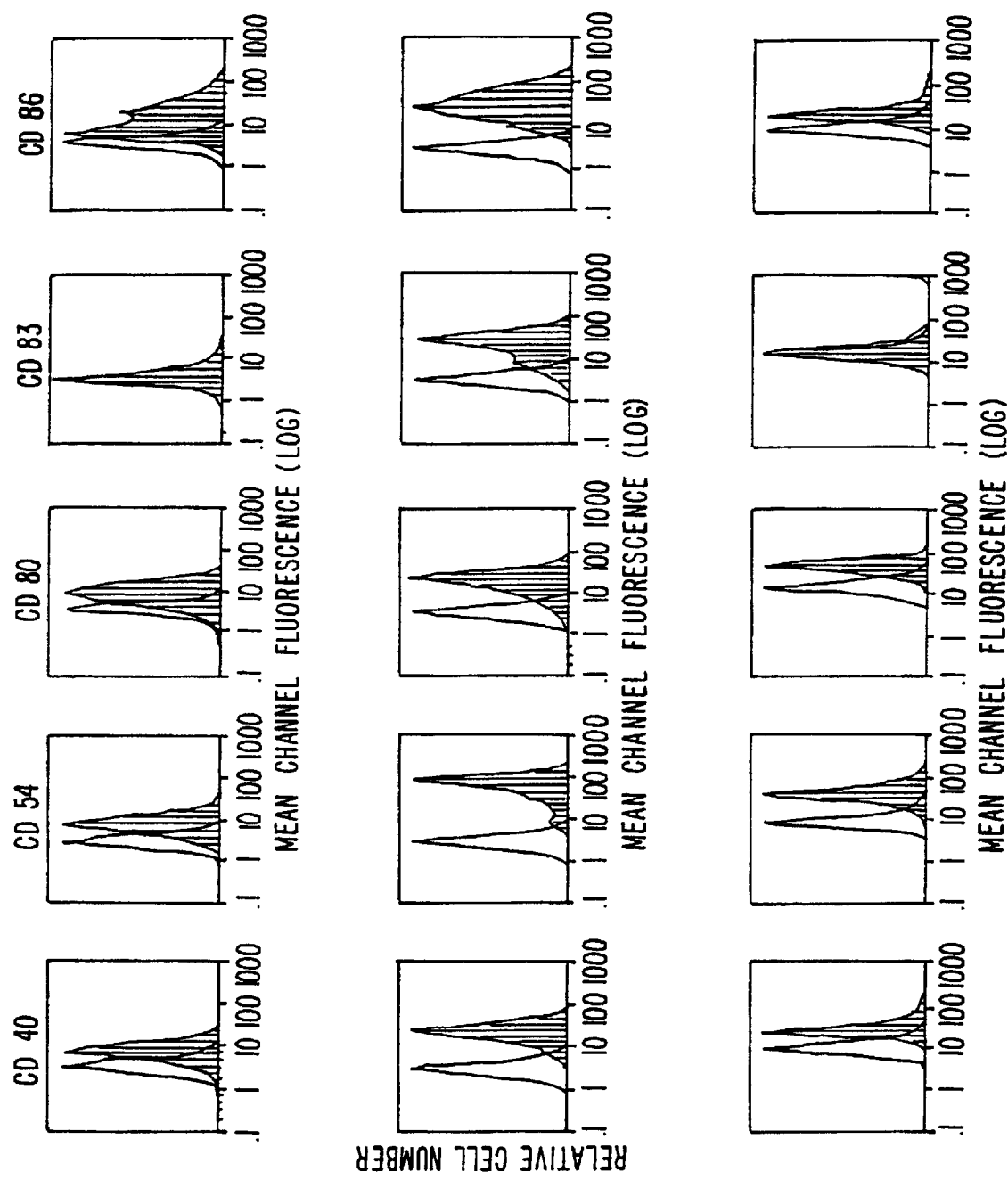

d 24 DCs TNF d22-24 d 24 DCs TNF d10-12 d 24 DCs TNF d10-12 & d22-24

METHODS AND COMPOSITIONS FOR MAKING DENDRITIC CELLS FROM EXPANDED POPULATIONS OF MONOCYTES AND FOR ACTIVATING T CELLS

CROSS REFERENCE TO RELATED APPLICATIONS

This application is a continuation-in-part of U.S. Ser. No. 60/047,348 "METHODS AND COMPOSITIONS FOR MAKING DENDRITIC CELLS FROM EXPANDED POPULATIONS OF MONOCYTES AND ACTIVATING T CELLS" Assigned to the National Institutes of Health, Inventors: Edward Nelson and Susan Strobl, filed May 21,1997. This application is entitled to and claims priority to U.S. Ser. No. 60/047,348, which is incorporated herein by reference for all purposes.

FIELD OF THE INVENTION

The invention relates to generation of dendritic cells from expanded populations of monocytes. These dendritic cells are potent antigen presenting cells which can mediate a variety of T cell responses. The invention relates to the fields of immunology, molecular biology, and medicine.

BACKGROUND OF THE INVENTION

T cells mediate most forms of cellular immunity, including cell lympholysis, delayed type hypersensitivity (DTH), transplantation rejection, and allograft rejection. An introduction to T cells and cell mediated immunity is found in Paul (1993) *Fundamental Immunology, Third Edition* Raven Press, New York, N.Y. and the references cited therein.

Typical T cells do not respond to free antigenic peptides. Some T cells interact with a specialized set of cell surface proteins (the class I and class II major histocompatibility complexes, or MHC) which present antigens on the surface of cells (T cells also recognize antigens in the context of other molecules). Cytotoxic and helper T cells are induced to proliferate by specialized antigen presenting cells, such as macrophage and dendritic cells, which present antigenic epitopes, such as peptides or carbohydrates, on their cellular surfaces in conjunction with MHC molecules. T cells are induced by these antigen presenting cells to recognize corresponding antigens expressed, e.g., on MHC antigens on the surface of target cells. T cells destroy these target cells, or induce other cells to destroy these target cells.

Certain T cells can recognize the antigen in the form of a polypeptide fragment bound to the MHC class I molecules on target cells, rather than the intact polypeptide itself. The polypeptide is endogenously synthesized by the cell, and a portion of the polypeptide is degraded into small peptide fragments in the cytoplasm. Some of these small peptides translocate into a pre-Golgi compartment and interact with class I heavy chains to facilitate proper folding and association with the subunit $\beta 2$ microglobulin. The peptide-MHC class I complex is then routed to the cell surface for expression and potential recognition by specific T cells. Investigations of the crystal structure of the human MHC class I molecule HLA-A2.1 indicate that a peptide binding groove is created by the folding of the $\alpha 1$ and $\alpha 2$ domains of the class I heavy chain (Bjorkman et al., (1987) *Nature* 329:506). Falk et al., (1991) *Nature* 351:290 have developed an approach to characterize naturally processed peptides bound to class I molecules. Other investigators have successfully achieved direct amino acid sequencing of the more abundant antigenic peptides in various HPLC fractions by conventional automated sequencing of peptides eluted from class I molecules (Jardetzky, el al. (1991) *Nature* 353:326 and mass spectrometry Hunt, et al., *Science* 225:1261 (1992). A review of the characterization of naturally processed peptides in MHC Class I is found in Rötzschke and Falk (1991) *Immunol. Today* 12:447.

Target T cells recognizing antigenic peptides can be induced to differentiate and proliferate in response, for example, to antigen presenting cells bearing antigenic peptides in the context of MHC class I and class II complexes. There are differences in the antigenic peptides bound to MHC class I and class II molecules, but the two classes of bound peptides share common epitopes within the same protein which enable a T cell activated by an antigen presenting cell to recognize a corresponding epitope in the context of MHC class I or II, or other cell surface molecules. MHC class I molecules on target cells typically bind 9 amino acid antigenic peptides, while corresponding MHC class II-peptide complexes have greater heterogeneity in the size of the bound antigenic peptide.

Dendritic cells are the most potent antigen presenting cells known, being capable of activating T cells, NK cells and other immune cells by presentation of peptides and carbohydrate antigens on the MHC class I and class II molecules on the surface of the cells. An extensive review of the origin, maturation and antigen presenting function of dendritic cells in reviewed in Banchereau and Schmitt (1995) *Dendritic Cells In Fundamental and Clinical Immunology Volume 2*, in *Advances in Experimental Medicine and Biology* (Back et al. eds), volume 378 Plenum Press, NY. A short review is found in Cella et al. (1997) *Current Opinion in Immunology* 9:10–16, and the references cited therein. See also, Hart (1997) *Blood* 90:3245 (1997); J. Banchereau and R. M. Steinman (1998) *Nature* 392: 245; Schuler et al. (1997) *Int Arch Allergy Immunol* 112:317–322; Rescigno et al. (1997) *Journal of Leukocyte Biology* 61:415–421, Clark (1997) *J. Exp. Med.* 185(3) 801–803, Sprent (1995) *Current Biology* 5(10): 1095–1097; Nair et al. (1995) *International Immunology* 7(4):679–688; Caux et al. (1995) *immunology Today* 16(1):2–4; Liu et al. (1996) *International Review of Cytology* 166:139–179, and O'Doherty et al. (1993) *J.Exp. Med.* 178:1067–1078, and the references cited in each article.

"Immature" and "mature" phenotypic subsets of dendritic cells have been characterized and methods for the isolation and/or generation of DCs have been described, including various conditions for generating "immature" and "mature" DC subsets. See, e.g., Steinman (1991) *Ann Rev Immunol* 9:271; Steinman et al. (1993) *Adv Exp Med Biol* 329:1; Schuler et al. (1997) *Int Arch Allergy Immunol* 112:317; Jaffe (1993) *Pediatric Pathology* 13:821. Peters, et al., (1996) *Immunology Today* 276:273; Herbst, et al. (1996) *Blood* 88:2541. Romani et al. (1996) *J Immunol Methods* 196:137. Cella et al. (1997) *Current Opinion Immunology* 9: 10. Morse, et al. (1997) *Annals of Surgery* 226:6; Santiago-Schwartz, et al. (1992) *J Leuk Biol* 52:274; Zhou and Tedder (1996) *Proc Natl Acad Sci USA*. 93:2588; C. Caux, et al. (1996) *J Exp Med* 184;695; C. Caux, et al. (1997) *Blood* 90:14589; Winzler, et al., (1997) *J Exp Med* 185:317. Sallusto and Lanzavecchia (1994) *J Exp Med* 179:1109.

A general introduction to the use of dendritic cells for immunotherapy is provided by Girolomoni et al. (1997) in *Immunology Today*. In addition to presenting antigens to T-cells and NK cells, dendritic cells stimulate T cell mitogenesis, e.g., by producing the T cell mitogen IL-12. See, e.g., Jonuleit et al. (1997) *Journal of Immunol.* 2610–2614.

Despite the clear value of dendritic cells for immunotherapy, problems remain in using dendritic cells for therapeutic applications. Primarily, dendritic cells are very rare in peripheral blood, making isolation of sufficient numbers of such cells for therapeutic applications impractical. For example, autologous therapies in which dendritic cells are isolated from a patient and loaded with a particular peptide or carbohydrate antigen for T cell activation are impractical in the absence of large numbers of dendritic cells. Accordingly, there exists a need in the art for a method of making dendritic cells which are capable of T cell activation, particularly in the context of autologous therapeutic approaches. This invention solves these and other problems.

SUMMARY OF THE INVENTION

The present invention derives, in part, from the surprising discovery that IL-3 cultured expanded populations of monocytes are suitable for in vitro differentiation into dendritic cells. Thus, the present invention overcomes problems of the prior art by providing an easy method of generating large numbers of dendritic cells, i.e., from cultured monocytes. This, in turn facilitates the use of dendritic cells to generate cell-mediated immune responses.

Accordingly, in one embodiment, the invention provides methods of differentiating monocytes into dendritic cells. In the methods, monocytes are incubated in the presence of IL-3, causing the monocytes to proliferate, yielding an expanded population of monocytes. The expanded population of monocytes is differentiated into dendritic cells, e.g., by culturing the expanded population of cells with GM-CSF and IL-4 (to produce baseline or Type I DCs) and, optionally, TNF-α, CD40 ligand, IL-1α or IL-1β (to produce "activated" or "type II" DCs). For example, when baseline DCs are incubated with TNF-α, an "activated" or "type II" dendritic cell, characterized by the expression of certain markers, results. It is surprisingly discovered that the effects of TNF-α are reversible and reinducible in human DCs. TNF-α transiently activates DCs to a heightened proinflammatory state. Similar effects are obvserved upon incubation with IL-1α or IL-1β and CD40 ligand; in certain applications, any of these cytokines, or a combination thereof, are preferred for making activated DCs. Slightly different phenotypes are observed when different cytokines are used for activation; for example, CD 40 ligand results in expression of IL-12 in DCs.

Monocytes are obtained from a variety of sources, such as leukapheresis of peripheral blood mononuclear cells from a patient, followed by elutriation of the isolated peripheral blood to provide isolated monocytes.

Typically, a peptide is loaded onto the surface of resulting dendritic cells for presentation to a T cell, resulting in proliferation of the T cell (as measured, e.g., in an MLR assay), in vitro or in vivo. Peptide is loaded by any of a variety of methods, including incubation of the peptide with the dendritic cell, incubation of a protein comprising the peptide with DC, transduction of DC (or the progenitor expanded monocyte population) with a gene encoding the peptide (or a protein comprising the peptide), or the like. Typical antigens for use as peptides are derived from those expressed in a target cell such as a transformed cell, a cancer cell, a bacterial cell, a parasitically infected cell or a virally infected cell, or the like. Examples include, but are not limited to, carbohydrates such as mucin, tumor antigens, peptides derived from a protein selected from the group consisting of HIV Gag, HIV Env, HER-2, MART-1, gp-100, PSA, HBVc, HBVs, HPV E6, HPV E7, tyrosinase, MAGE-1, trp-1, mycobacterial antigens, and CEA, as well as many others. Tumor antigens suitable for presentation include, but are not limited to, c-erb-β-2/HER2/neu, PEM/MUC-1, Int-2, Hst, BRCA-1, BRCA-2, truncated EGFRvIII, MUC-1, CEA, p53, ras, RK, Myc, Myb, OB-1, OB-2, BCR/ABL, GIP, GSP, RET, ROS, FIS, SRC, TRC, WTI, DCC, NF1, FAP, MEN-1, ERB-B1 and idiotypic immunoglobulins (e.g., from a B cell of a non-Hodgkin's lymphoma patient). Ordinarily, the antigens are expressed on the surface of the target cell in the context of an MHC class I molecule (but peptide is also presented in other contexts), which is recognized by the T cell. The antigen presenting activity of dendritic cells is enhanced by co-culture with certain cytokines such as TNF-α or IL-1α or IL-1β. In addition, the cytokines produced by dendritic cells (e.g., IL-12) provide therapeutic benefits, by stimulating T cells and NK cells.

In ex vivo therapeutic applications, T cells are isolated from a patient, activated in vitro, and re-introduced into the patient. Similarly, dendritic cells made from monocytes isolated from a patient and expanded in culture are differentiated in vitro into dendritic cells, which are used to activate T cells in vitro, or by re-introduction into the patient.

It will be appreciated that the availability of high numbers of dendritic cells provide methods of activating a T cell. In basic form, the method includes contacting the T cell with a dendritic cell made according to the methods of the invention, e.g., in culture, or in vivo wherein the dendritic cell is made by the method of claim 1, thereby producing an activated T-cell. Activated T cells are useful for the treatment of a variety of disorders, including cancer, viral, bacterial or parasitic infection. Activated T cells are competent to kill tumorigenic or infected cell, or direct a helper response against such cells.

Cell cultures for making recombinant dendritic cells are provided. These cultures include an expanded population of monocytes, and, typically cytokines such as IL-4 and GM-CSF. The cultures optionally include other cytokines such as IL-3 or TNF-α, or IL-1α or IL-1β. Depending on the mammal from which the cell culture is selected, the cytokines are appropriately derived from the particular species. For example, where the cells are of human origin, hGM-CSF is typically used. Where the cells are of murine origin, mGM-CSF is used. However, it will be recognized that many such proteins are active outside of the particular mammal from which they are derived.

Diagnostic methods and methods for assessing whether a target antigen is an appropriate target for a T cell are provided. For example, T cell mediated anti-cancer cell (or other target cell) activity of a target antigenic peptide is measured in one embodiment. In this embodiment, a dendritic cell is provided from an expanded population of monocytes. The dendritic cell comprises the antigenic peptide. A T cell is contacted with the dendritic cell (from an autologous source), thereby providing an activated T cell with specificity for the antigenic peptide. The cancer cell is contacted with the activated T cell and the effect of the activated T cell on the cancer cell is monitored, thereby detecting the anti-cancer cell activity of the target antigenic peptide. It will be appreciated that essentially similar methods are practiced to detect the activity of target antigens from infected cells such as bacterial cells, virally infected cells, parasitically infected cells, or the like. Essentially any protein or peptide is presented to the T cell. For example, in one embodiment, the antigenic peptide is derived from HER-2, and the cancer cell is a breast cancer cell. In another class of embodiments, the antigenic peptide is derived from a protein selected from the group consisting of MART-1 and gp-100, wherein the cancer cell is a melanoma cell. In other embodiments, the antigenic peptide is derived from CEA and the cancer cell is a colon cancer cell. Similar sets of tumor antigens and tumors, or infectious epitopes and infected cells are similarly screened. Depending on the assay format, the activated T cell and target cell are reacted in vitro or in vivo.

Methods of killing a target cell are provided. In the methods, the target cell is contacted with an activated T cell, wherein the T cell is activated by contacting the T-cell with a dendritic cell made from a population of monocytes expanded in the presence of IL-3. The T cells are contacted with the target cell in vitro or in vivo. Typical target cells include infected cells such as bacterially infected, virally-infected, or parasitically infected cells, as well as tumor cells.

Pharmaceutical compositions are provided. The compositions have a pharmaceutically acceptable carrier and a population of at least about $10^5$ dendritic cells, and often at least about $10^6$ cells, occasionally $10^7$ cells, or more, made from a population of monocytes expanded by culture with IL-3, which dendritic cells present a subsequence of a heterologous protein, which population of dendritic cells is competent to activate T cells to kill a target cell in vitro. Typically, the dendritic cells are made from an expanded population of monocytes by incubation with TNF-α, IL-4 and GM-CSF. In one preferred embodiment, the dendritic cells are primarily "activated" or "type II" dendritic cells. In some aspects, the population of dendritic cells is competent to activate said T cells against said target cell in vivo. Examples of heterologous protein include HER-2, MART-1, gp-100, PSA, HBVc, HBVs, tyrosinase, MAGE-1, trp-1 and CEA. In other aspects, DC stimulate immune cells such as NK cells, e.g., by secreting cytokines such as IL-12.

Finally, it should be appreciated that the invention provides compositions having a population of isolated monocytes and IL-3. In one preferred embodiment, IL-3 is present at a concentration of about 10 ng/ml.

BRIEF DESCRIPTION OF THE DRAWING

FIGS. 5A–5F are a series of graphs showing log mean channel fluorescence versus relative cell number.

FIGS. 8A–8F, panels A-F is a series of graphs showing relative cell number versus mean channel fluorescence (log).

DEFINITIONS

Figure 1A:
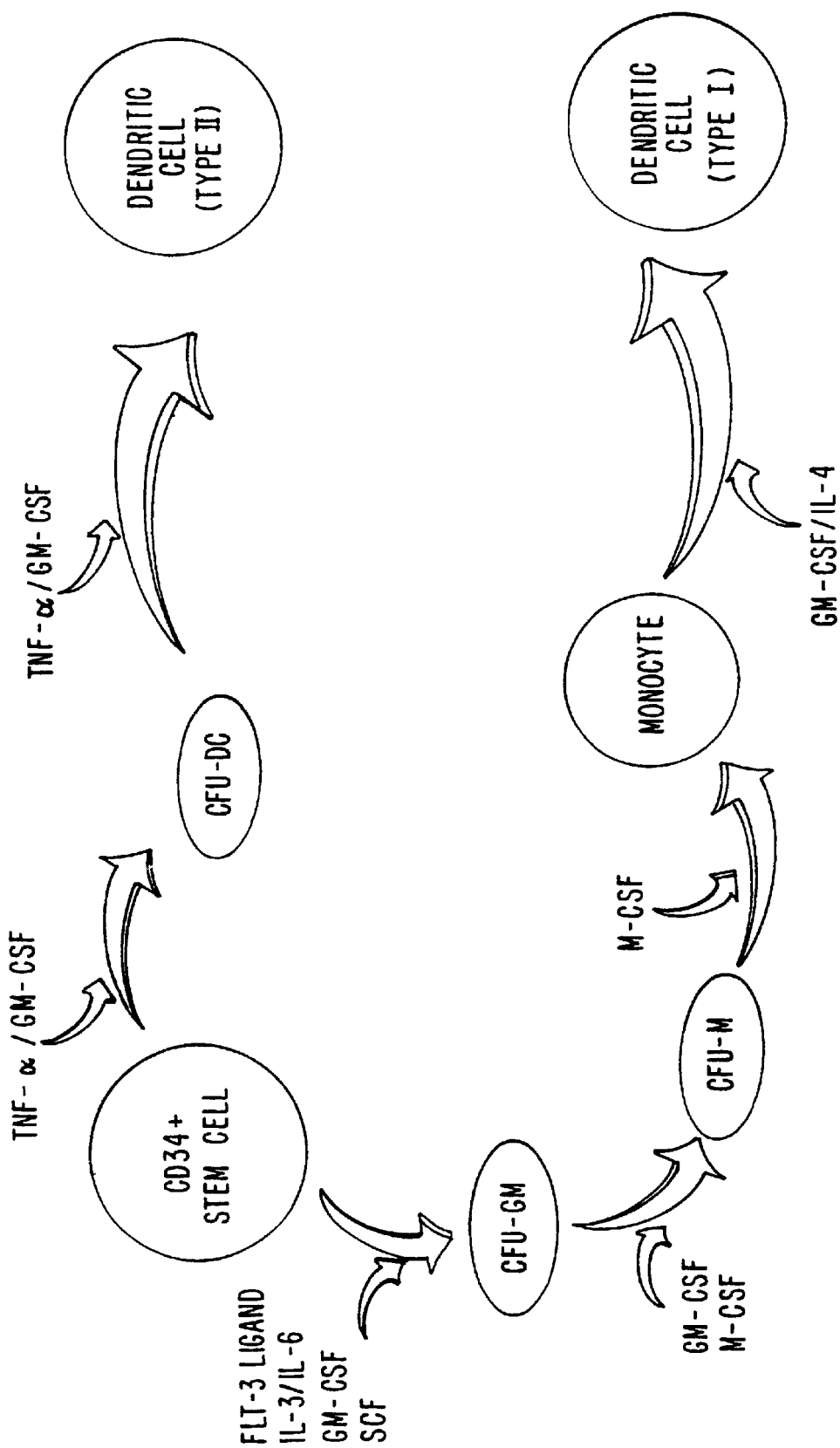
FIGS. 1A–1B, panels A and B show dendritic cell pathways for generation of dendritic cells in vivo.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are described. For purposes of the present invention, the following terms are defined below.

A "dendritic cell" (DC) is an antigen presenting cell (APC) which can be derived from a monocyte cell by the methods described herein. As shown herein, monocytes can be differentiated into DC in vitro. The dendritic cell has a characteristic morphology with thin sheets (lamellipodia) extending from the dendritic cell body in several directions. Several phenotypic criteria are also typical, but can vary depending on the source of the dendritic cell. These include high levels of MHC molecules and costimulatory molecules (e.g., B7-1 and B7-2), and a lack of markers specific for granulocytes, NK cells, B cells, and T cells. Many dendritic cells express certain markers; for example, some Human dendritic cells selectively express CD83, a member of the immunoglobulin superfamily; see also, Zhou and Tedder (1995) *Journal of Immunology* 3821–3835. Many dendritic cells are characterized by expression of CD1a. Dendritic cells are able to initiate primary T cell responses in vitro and in vivo. These responses are antigen specific. Dendritic cells direct a strong mixed leukocyte reaction (MLR) compared to peripheral blood leukocytes, splenocytes, B cells and monocytes. Dendritic cells are optionally characterized by the pattern of cytokine expression by the cell; see also, Zhou and Tedder (1995) *Blood* 3295–3301.

"IL-3" is a cytokine commercially available in a variety of forms. For example human recombinant IL-3 is available from peproTECH., inc. Rocky Hill, N.J. IL-3 in slightly different forms is available from a variety of suppliers, or can be purified from a variety of biological sources. Recombinant human IL-3 is preferred. Minor modifications of naturally occurring IL-3, particularly IL-3, are encompassed by the term, unless otherwise indicated. For example, recombinant conservative substitution of one or a few (typically less than 10%) naturally occurring amino acids with a similar amino acid in the IL-3 protein are considered IL-3 for purposes of this disclosure. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). See also, Creighton (1984) Proteins W. H. Freeman and Company.

"Monocytes" are well characterized cells from the peripheral blood known to persons of skill. Monocytes are isolated according to the methods described herein, and can be differentiated into a DC under selected culture conditions, e.g., by culture with IL-4 and GM-CSF.

A "target cell" or a "T cell targeted cell" is a cell which expresses an antigenic epitope on the surface of the cell. Optionally, the epitope is recognized in the context of an MHC molecule. T cells recognize antigenic epitopes, e.g., in the context of MHC (or other cell surface molecules) and kill the target cell, either by cell lysis, or by recruiting other immune cells to the site of the target cell by releasing cytokines. T cells which recognize the antigenic molecule are induced to proliferate in response to antigen presenting cells (e.g., dendritic cells) which express corresponding antigenic peptides.

A "target protein" is a protein which comprises antigenic peptide subsequences. These subsequences are expressed on target cells, e.g., in the context of MHC or other cell surface molecules (e.g., a cell surface protein). T cells recognize epitopes formed by the peptide, or by the binding of surface protein such as an MHC protein to these peptide subsequences and typically lyse the cell (a CTL response), or recruit and activate other immune cells (e.g., macrophage, NK cells or CTLs) to the site of the target cell, thereby helping to kill the target cell.

An "immunogenic peptide" or "antigenic peptide" is a peptide which is recognized by an activated T cell, or which binds an MHC (or other cell surface molecule) to form an epitope recognized by a T cell, thereby inducing a cell mediated response upon presentation to the T cell. Thus, some antigenic peptides are capable of binding to an appropriate MHC molecule and inducing a cytotoxic T cell response, or helper response, e.g., cell lysis or specific cytokine release against the target cell which binds or expresses the antigen, or recruitment of cells to the target cell for subsequent lysis.

A "cell receptor ligand" is a biological molecule which binds to a cell receptor (which is optionally an extracellular receptor or an intracellular receptor), thereby activating the receptor.

The terms "isolated" or "biologically pure" refer to material which is substantially or essentially free from components which normally accompany it as found in its naturally occurring environment. The isolated material optionally comprises material not found with the material in its natural environment (e.g., buffers, surfactants, anti-oxidants, bactericidal components or the like).

The term "nucleic acid" refers to a deoxyribonucleotide or ribonucleotide polymer in either single- or double-stranded form, and, unless otherwise limited, encompasses known analogues of natural nucleotides that hybridize to nucleic acids in a manner similar to naturally occurring nucleotides. Unless otherwise indicated, a particular nucleic acid sequence optionally includes the complementary sequence thereof. A nucleic acid "encodes" another nucleic acid where it is the same as the specified nucleic acid, or complementary to the specified nucleic acid.

The term "operably linked" refers to functional linkage between a nucleic acid expression control sequence (such as a promoter, or array of transcription factor binding sites) and a second nucleic acid sequence (such as a nucleic acid for a heterologous protein), wherein the expression control sequence directs transcription of the nucleic acid corresponding to the second sequence.

"Optimal differentiation" of a population of monocytes into a population of dendritic cells in the context of a titration experiment for a particular cytokine refers to achieving the highest percentage of dendritic cells in the population after incubation with the cytokine. Typically, titrations include systematically varying cytokine concentration and/or incubation time and comparing the results of the different concentrations or incubations.

A "primary" monocyte is a monocyte isolated from a patient, or a culture of such monocytes. A "primary dendritic cell" is a dendritic cell taken from a patient, or derived by differentiation of a monocyte or monocyte culture taken from a patient. A primary dendritic cell in an established cell culture which has undergone many serial passages in culture is not a primary dendritic cell, but may be referred to as an established dendritic cell or established dendritic cell culture. A "primary cultured dendritic cell" is a dendritic cell differentiated from a culture of primary monocytes.

A "NK" or "natural killer" cell (sometimes referred to as a large granular lymphocyte, or "LGL") is a cell derived from bone marrow which mediates a non-MHC restricted cytolytic response against cells.

A "transformed" cell when referred to as a target for therapy in the present invention refers to a cell exhibiting abnormal growth, typically in a mammalian organism, such as a tumor cell, a malignant cell, a neoplastic cell, a pre-neoplastic cell or the like.

DETAILED DISCUSSION OF THE INVENTION

Dendritic cells (DC) are highly potent antigen presenting cells that are capable of activating quiescent T-cells, and which stimulate effective anti-tumor immune responses. Dendritic cells have been effective against established tumors as therapeutic agents. Dendritic cells have several advantages over other forms of anti-tumor immunization, such as recombinant viral vaccines, in that the immunization method is entirely autologous, and therefore no problems with pre-existing neutralizing antibodies are expected, even with repeated dosing. In addition, dendritic cell immunizations can be used in combination with other methods of immunization.

One significant problem prior to the present invention was obtaining sufficient quantities of dendritic cells for therapeutic purposes. The present invention overcomes this problem by providing expanded populations of monocytes and differentiating the monocytes into dendritic cells. In particular, it was surprisingly discovered that IL-3 was suitable for the expansion of monocytes in a manner which still permitted differentiation of the monocytes into dendritic cells. Prior art expansion methods for expanding monocytes relied primarily on incubation with stimulatory agents such as M-CSF or LPS; however, it was discovered that these simulators were not suitable for purposes of the present invention, because monocytes expanded by culture with these cytokines could not be differentiated into dendritic cells. To overcome this previously unknown problem, several cytokine combinations for expansion of monocytes followed by differentiation into dendritic cells were attempted. It was discovered that IL-3 expanded monocyte populations could be differentiated into dendritic cells in vitro using IL-4 and GM-CSF. Furthermore, it was found that dendritic cells made from expanded populations of monocytes from a cancer patient could be loaded with appropriate antigens and used to stimulate a T-cell response, as measured, e.g., in a lymphocyte proliferation assay.

Antigens from a variety of pathogens/diseased cells on a number of potential target cells are known to mediate cell mediated immune responses to the target cells, and it is expected that one of skill is thoroughly familiar with the identity of many such antigens. T cells recognizing such epitopes are stimulated to proliferate in response to antigen presenting cells such as dendritic cells, including the dendritic cells made according to the methods of the invention. Examples of antigens include prostate specific antigen (PSA), hepatitis B core and surface antigens (HBVc, HBVs) hepatitis B or C antigens, Epstein-Barr virus antigens, melanoma antigens (e.g., MAGE-1, MART-1 and gp 100), Colon cancer antigens (e.g., CEA), breast cancer antigens (e.g., HER-2) Leukemia antigens, human immunodeficiency virus (HIV) antigens, herpes virus antigens (see, e.g., Manickan et al. (1997) *Journal of Leukocyte Biology* 61:125–132 for an example of HSV transduced dendritic cell immunogenicity), hepatitis (e.g., A, B, or C) tyrosinase, trp-1, Malarial antigens (e.g., proteins derived from Plasmodium), mycobacterial antigens (e.g., for TB or leprosy) or human papilloma virus (HPV) antigens.

In preferred embodiments, monocytes are differentiated into dendritic cells. One of skill will appreciate that many therapeutic applications are improved by administering autologous cells to a patient, i.e., cells which were originally isolated from the patient, or which are derived from a patient by culturing isolated cells. These autologous cells are less likely to cause immune complications upon reintroduction into the patient.

As discussed, DC play a crucial role in the human immune response, acting as one of the most potent antigen presenting cells (APC) known. The blood is one of the most readily available tissues for studying immune responses; however, dendritic cells are found in extremely low numbers in the circulating peripheral blood, <1%, making evaluation of their true lineage and functional capacity difficult. To date, there has been no lineage specific cell surface marker defined. Isolation and identification of dendritic cells has been dependent on their physical characteristics, a compilation of cell surface markers, and their ability to perform as processors and presenters of antigen (Ag) in functional assays. Mature DC are large, low density cells with multiple dendritic (branching) processes. With >99% of DC residing in tissues other than peripheral blood, DC precursors have been the source of dendritic cells for study.

Figure 1B:
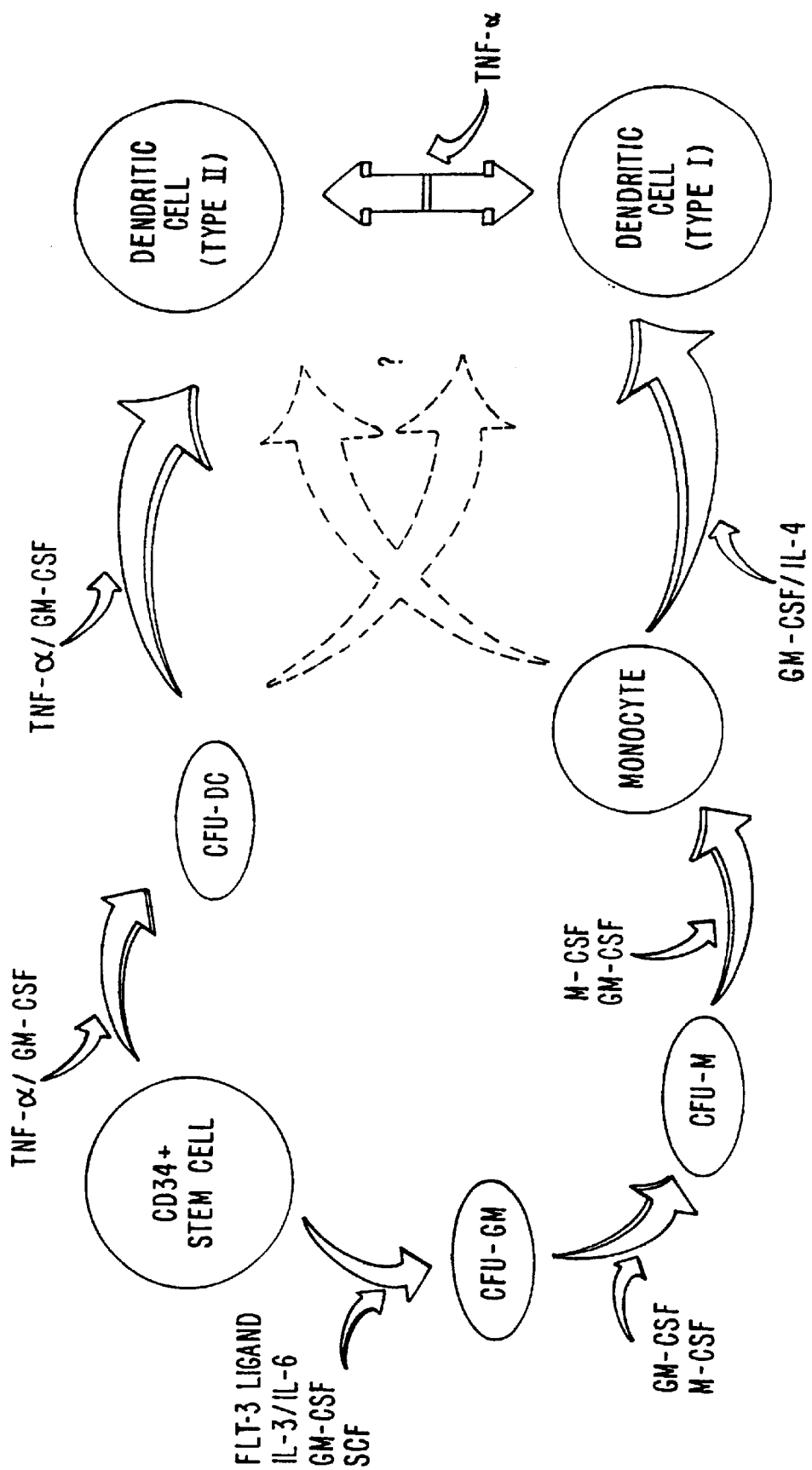

It is generally believed DC precursors are ultimately of bone marrow origin (CD34$^+$ progenitor cells), however, the maturation pathway(s) to a functional DC have not been clearly defined. The cytokines granulocyte/macrophage-colony stimulating factor (GM-CSF) and tumor necrosis factor (TNF-α) are thought to produce "mature" dendritic cells which are extremely efficient at presenting antigen and stimulating T cells (See, FIG. 1, panels A and B). As shown herein, it is more accurate to consider dendritic cells in terms of "baseline" and "activated" as, for example, TNF-α, has a reversible effect upon dendritic cell cytokine expression. Reports suggest that monocytes (MO) cultured with GM-CSF and Interleukin 4 (IL-4) may develop characteristics of immature or "baseline" (Type 1) dendritic cells which are proficient at processing antigen and somewhat less potent simulators of T cells. To date, the procedures to isolate dendritic cells and/or their precursors from peripheral blood have been involved and time consuming, using adherence, negative and positive selection with antibodies for panning or sorting, magnetic bead depletion and tissue culture. The cell numbers obtained after these isolation procedures are small and therefore limiting for further study or use. As set forth below, this invention provides the ability to generate large numbers of peripheral blood monocytes by simple elutriation (counter-flow centrifugal separation). It is demonstrated that the resulting MO can be differentiated into dendritic cells with either baseline (Type I) or activated (Type II) phenotype and/or function. The generation of large numbers of baseline and activated dendritic cells from a single donor allows for the study of their characteristics and functions and provides for the application of their use in a clinical therapy setting, e.g., in autologous therapeutic procedures.

Expansion of Monocytes Using IL-3

Monocytes are isolated from a patient (or normal cell donor) using standard techniques. For instance, in one preferred embodiment, monocytes are isolated by Ficoll Hypaque centrifugation followed by centrifugal elutriation, e.g., following leukapheresis or Buffy coat isolation.

The process of centrifugal elutriation is well known. In brief, two opposing forces, centrifugation and elutriation, combine to create a gentle means of separating cells and other particles by sedimentation rate. The separation takes place in a funnel-shaped elutriation chamber in a centrifugal rotor. While the rotor is spinning in the centrifuge, a suspension of cells is pumped from outside the centrifuge into the rotor to the narrow (centrifugal) end of the elutriation chamber at a preset selected flow rate. As the fluid travels into the chamber, its velocity decreases as the chamber walls become wider, creating a velocity gradient from one end of the chamber to the other.

Each cell in the chamber is acted upon by two opposing forces: the centrifugal force field (causing it to move away from the center of rotation) and fluid velocity (causing it to move toward the center of rotation). Cells of different sizes or sedimentation rates migrate to positions in the velocity gradient where the effects of the two forces are balanced with their individual sedimentation rates. The smallest cells migrate toward the widest part of the chamber where the centrifugal force field and the velocity are low. Larger cells remain near the narrow portion of the chamber where the centrifugal force field and the velocity are high.

The area farthest into the chamber where cells are suspended in equilibrium is called the elutriation boundary. Small cells having sedimentation rates too low to be a equilibrium at the elutriation boundary are washed out of the chamber, up through the rotor, and out to a collection vessel. Cells remaining in suspension at the elutriation boundary are elutriated subsequently.

By increasing the flow rate in gradual steps, successive fractions of increasingly large or dense cells can be washed out of the rotor and collected. Continued incremental increase of the slow rate finally elutriates all cells from the chamber. Elutriation chambers are available in different sizes and shapes, depending on the desired application.

In an alternate embodiment, the cells are centrifuged on Ficoll-Hypaque, or a similar system. T and B cells are removed by incubation appropriate antibodies, e.g., with M-450 Pan B/CD19 and M-450 Pan T/CD2 dynabeads (Dynal, Oslo Norway) at a 1:1 ratio (cell:CD19 bead:CD2 bead). See also, Chapuis et al. (1997) *Eur. J. Immunol.* 27:431–444; Zhou and Tedder (1996) *PNAS* 93:2588–2592; Xu el al. (1995) *Dendritic Cells in Fundamental Clinical Immunology*, Volume 2, page 75–78 (Banchereau and Schmitt eds.), Plenum Press, NY; Kiertscher and Roth (1996) *Journal of Leukocyte Biology* 59:208–218, and Tsai et al. (1997) *The Journal Of Immunology* 1797–1802.

The isolated monocytes are cultured with IL-3 for at least 3 days, and preferably less than 10 days. Optimal subsequent differentiation into dendritic cells was observed with 5–7 days of culture with IL-3.

In one example, monocytes were cultured at 1×10$^6$ cells/ml in RPMI 1640 (BioWhittaker, Walkersville, Md.) supplemented with L-glutamine (2 mM), sodium pyruvate (1 mM), non-essential amino acids (0.1 mM), penicillin (50 units/ml), streptomycin (50 ug/ml), BME (50 mM) and 10% fetal calf serum. IL-3 (10 ng/ml) was added at day 0 and the cells were cultured for 5–7 days to obtain proliferating monocytes. At the end of the 5–7 day culture period, the IL-3 was removed from the culture by pelleting the cells and removing the supernatant, then washing the cell pellet once more with phosphate buffered saline (PBS). The washed cells were then placed in culture with GM-CSF and IL-4 as indicated below. See also, Example 1.

Titration experiments were performed to determine the optimal dose of IL-3 for monocyte expansion. Preferred concentrations ranged from about 0.1–100 ng/ml, generally about 1–100 ng/ml, with good expansion of monocytes observed using IL-3 from about 5–50 ng/ml; a generally preferred dose of generally about 10 ng/ml was typically used.

Differentiation of Monocytes into Dendritic Cells

IL-3 expanded populations of monocytes are differentiated by culturing the cells with GM-CSF and IL-4. See also, Sallusto and Lanzaveccia (1994) *J.Exp. Med.* 179:1109–1118. Chapuis et al. (1997) *Eur. J. Immunol.* 27:431–444; Zhou and Tedder (1996) *PNAS* 93:2588–2592, and Jonuleit et al. (1997) *The Journal of Immunology* 2610–2614. Optionally, TNFα is added to potentiate the antigen presenting activity of DC.

In one example, monocytes were cultured at $1 \times 10^6$ cells/ml in RPMI 1640 (BioWhittaker, Walkersville, Md.) supplemented with L-glutamine (2 mM), sodium pyruvate (1 mM), non-essential amino acids (0.1 mM), penicillin (50 units/ml), streptomycin (50 ug/ml), BME (50 mM) and 10% fetal calf serum. GM-CSF (100 u/ml) and IL-4 (50 ng/ml) were added at day 0 and the cells were cultured for 10–12 days to obtain Type I, or "baseline" DC. TNF-α (20 ng/ml) was added to aliquots of Type I (baseline) cultures at 10–12 days for 48 hours to obtain "activated" or "Type II" DC. Cultures were fed every 6–7 days by removing ½ of the culture volume and adding an equal volume of fresh media containing GM-CSF and IL-4 for the entire culture volume.

Loading Peptides on Dendritic Cells.

Proteins or peptide fragments which are differentially expressed in cancers, such as those associated with melanoma (e.g., MART-1, gp100, or tyrosinase; See, Zhai, et al., *J. Immunol.*, 156(2):700–10 (1996); Kawakami, et al., *J. Exp. Med.*, 180(1):347–52 (1994); and Topalian, et al., *Proc. Natl. Acad. Sci. USA*, 91(20):9461–5 (1994)) are beneficially loaded onto the DC of the invention for antigen presentation to T cells. Similarly, proteins associated with breast cancer (e.g., c-erb-2, bc1-1, bc1-2, vasopressin related proteins; see, North, et al., *Breast Cancer Res. Treat.*, 34(3):229–35 (1995); Hellemans, *Br. J. Cancer*, 72(2):354–60 (1995); and Hurlimann, et al., *Virchows Arch.*, 426(2):163–8 (1995)); and other carcinomas (e.g., c-myc, int-2, hst-1, ras and p53 mutants, prostate-specific membrane antigen (PSMA) and papiloma virus protein L1; see, Issing, et al., *Anticancer Res.*, 13(6B):2541–51 (1993); Tjoa, et al., *Prostate*, 28(1):65–9 (1996); Suzich, et al., *Proc. Natl. Acad. Sci. USA*, 92(25):11553–7 (1995); and Gjertsen, et al., *Lancet*, 346(8987):1399–400 (1995)) are beneficially loaded. Choudhury et al. (1997) *Blood* 4:1133–1142 describe the use of leukemic dendritic cells for autologous therapy against chronic myelogenous leukemia (CML); accordingly, it will be appreciated that leukemia antigens are suitably loaded onto the DC of the invention.

In one embodiment, an HPV protein is a target protein presented by a DC of the invention. The principle transforming genes of the cancer associated HPV's are E6 and E7 (Munger, et al. (1992) *Cancer Surveys* 12: 197–217). The E6 oncoprotein targets the proteolysis of p53 through the ubiquitination pathway (Scheffner et al. (1990) *Cell* 63: 1129–1136), whereas the E7 protein binds the retinoblastoma protein (Dyson et al. (1989) *Science*, 243: 934–937) and related proteins p107 and p130 (Dyson et al. (1992) *J. Virol.* 66: 6893–6902), and in so doing releases E2F, a transcription factor, which transactivates several proliferation associated genes (Chellappan et al. (1992) *Proc. Natl. Acad. Sci. USA*, 89: 4549–4553). The remainder of the early region encodes the E2 transactivator/repressor, the E1 protein which binds to the origin of replication, the E4 protein, which has been shown to dissociate actin intermediate filaments, and the E5 protein, which increases the activity of both the EGF or PDGF receptors (Howley, (1989) *Papillomaviruses and Their Replication*, p. 1625–1650. In Fields et al. (ed.) *Virology*, 2nd Edition. Raven Press, New York).

Progression of HPV disease is associated with changes in the state of the viral genome and in patterns of viral transcription that may contribute to the development of malignancy. In condylomas, papillomas and mild/moderate dysplasias, the virus is episomal (Crum et al. (1984) *New Engl. J. Med.*, 310: 880–883; Cullen et al. (1991) *J. Virol.* 65: 606–612), and the entire early region is expressed (Shirasawa et al. (1988) *J. Virol.* 62: 1022–1027). In high grade dysplasias and in cancers, the viral DNA is integrated into the host genome. Integration frequently occurs in the E1/E2 ORF, disrupting the early region downstream of the E7 coding region, and potentially leading to deregulated expression of the E6 and E7 oncoproteins, due to the absence of E2 transcriptional regulation (Baker et al. (1987) *J. Virol.* 61: 962–971; Schwarz et al. (1985) *Nature*, 314: 111–114; Smotkin, et al. (1986) *Proc. Natl. Acad. Sci. USA*. 83: 4680–4684). These changes in viral structure and expression patterns during clinical progression suggest that the functions of the viral early region initiate cellular proliferative and dysplastic changes, whereas the E6 and E7 oncoproteins may be sufficient to maintain high grade dysplasia and malignancy. Any of these proteins are suitable targets for presentation by DCs of the invention. Other Tumor antigens suitable for presentation include, but are not limited to, c-erb-β-2/HER2/neu, PEM/MUC-1, Int-2, Hst, BRCA-1, BRCA-2, truncated EGFRvIII, MUC-1, CEA, p53, ras, RK, Myc, Myb, OB-1, OB-2, BCR/ABL, GIP, GSP, RET, ROS, FIS, SRC, TRC, WTI, DCC, NF1, FAP, MEN-1, ERB-B1. See also, *Cell* (1991) 64:235–326.

In one embodiment, tumor antigens are stripped off of tumor cells (e.g., with a mild acid wash). DCs of the invention are pulsed with the resulting mixture of tumor peptides and used for T cell activation. An example of the tumor stripping/dendritic cell presentation method is found in Zitvogel ,t al. (1996) *J. Exp. Med* 183:87–97. Similarly, bacterially, virally or parasitically infected cells are striped of antigen and the resulting peptide mixture used to pulse DCs.

Alternatively, tumor cells can be cloned or grown in culture; tumor antigens can be isolated from these cells, or the genes encoding, e.g., autologous tumor antigens can be cloned and overexpressed using standard techniques.

A variety of viral antigens are suitable for peptide loading. For example, the human immunodeficiency virus (HIV), a member of the lentivirus genus of retroviruses, is the causative agent of acquired immunodeficiency syndrome (AIDS) (review in Gonda, M. A., *Ann. N.Y. Acad. Sci.*, 724:22–42 (1994); Gonda, et al., *Control of Virus Diseases* (Kurstak, E. Ed.), pp. 3–31 (1992); Gallo, R. C., *J. Infect Dis.*, 164:235–243 (1991); Levy, J. A., *Microbiol. Rev.*, 57:183–289 (1993)). In the initial phase of infection, HIV replicates rapidly and large quantities of virus are shed from infected cells; this is accompanied by destruction of effector cells (CD4+ lymphocytes and, in some cases, macrophage) important in developing a competent immune response (Daar, N., *Engl. J. Med.*, 324:961–964 (1991); Graziosi, et al., *Proc. Natl. Acad. Sci. USA*, 90:6405–6409 (1993); Borrow, et al., *J. Virol.*, 68:6103–6110 (1994); Pantaleo, et al., *Nature* (London), 370:463–467 (1994)). The initial viremia passes into a subacute phase in which the activated immune system has apparently exerted some control over virus spread (Pantaleo, supra; Koup, et al., *J. Virol.*, 68:4650–4655 (1994)). In the majority of HIV cases, the subacute phase of infection progresses to severe disease, which includes a depletion of CD4+ lymphocytes and the subsequent onset of opportunistic infections and AIDS. A small proportion of HIV-infected individuals appears to have a reduced virus load suggesting effective immunological control of the virus (Cao, et al., *N. Engl. J. Med.*, 332:201–208 (1995)). Cytotoxic T-lymphocytes (CTLs) and helper T cells specific for HIV Gag and Env antigens are of key importance in inhibiting virus spread and delaying pathogenesis. See also, Klein, et al., *J. Exp. Med.*, 181:1365–1372 (1995); McFarland, et al., *J. Infect. Dis.*, 167:719–723 (1993)). HIV is a protein-encapsulated positive-sense RNA virus that buds from the infected cell membrane. Its genome contains the obligate gag, pol and env structural genes flanked by the long terminal repeats, as well as a number of nonstructural regulatory genes (Gonda, et al., *Control of Virus Diseases* (Kurstak, E. Ed.), pp. 3–31 (1992); Levy, J. A., *Microbiol. Rev.*, 57:183–289 (1993)). The gag gene encodes the Gag precursor, Pr55. The pol gene encodes proteins with enzymatic function (protease, reverse transcriptase, and endonuclease/integrase), while the env gene encodes the envelope glycoprotein precursor (gp160). The HIV virion can be divided into two basic morphologic components: the viral core and envelope. The viral core consists predominantly of gag- and pol- encoded proteins and the viral RNA. In immature virions, the core consists primarily of uncleaved Pr55. Upon maturation of the virus, the viral protease cleaves Pr55 and products of pol into functional domains important in virus entry and replication. Pr55 is processed into the matrix (p17$^{Gag}$), capsid (p24$^{Gag}$), nucleocapsid (p7$^{Gag}$) and p6$^{Gag}$ proteins. The viral envelope consists of a lipid bilayer derived from the cell surface membrane into which gp160 is specifically concentrated. gp160 is cleaved by cellular proteases into the surface glycoprotein, gp120, which interacts with the cellular receptor, and the transmembrane glycoprotein, gp41, which anchors gp120 to the plasma membrane (Gonda, et al., *Control of Virus Diseases* (Kurstak, E., Ed.), pp. 3–31 (1992)). Any of these proteins, or others encoded by the virus, are optionally presented on the surface of the DC of the invention, thereby causing a CTL or helper response against T cells (or other cells such as macrophage, for macrophage tropic HIV infections) infected with HIV. A primary proliferative response to Gag p24 peptides against HIV mediated by DCs was shown by Bedford et al. (1997) *Journal of Acquired Immune Deficiency Syndromes and Human Retrovirology* 14:301–306. The peptides used by Bedford et al. are, therefore, suitable for loading onto the DC of the present invention for presentation to T cells during autologous therapy. Bohm et al. (1995) *Journal of Immunology* 3313–3321 describe the presentation of hepatitis surface antigen (HBs-Ag) on dendritic cells; similarly, dendritic cells of the invention can present hepatitis antigens.

"Mycobacteria" include any bacteria of the genera Mycobacterium (family Mycobacteriaceae, order Actinomycetales) and includes *Mycobacterium tuberculosis, Mycobacterium avium complex, Mycobacterium kansasii, Mycobacterium scrofulaceum, Mycobacterium bovis* and *Mycobacterium leprae*. These species and groups and others are described in Baron, S., ed. *Medical Microbiology*, 3rd Ed. (1991) Churchill Livingstone, N.Y., which is incorporated herein by reference. Mycobacteria are the causative agent for a wide variety of disorders. Mycobacterium-infectable cells include macrophages, macrophage-type cells and other cell types which either under healthy or pathological conditions may engulf mycobacteria or be invaded by mycobacteria and thereby become infected, including macrophages, Kupffer cells, histiocytes, microglial cells, alveolar macrophages, cell lines derived from macrophages and also including primary cell cultures or cell lines having the characteristic properties or markers of macrophages. In general, proteins expressed by mycobacteria and mycobacterially infected cells in the context of MHC are attractive targets for cell mediated therapies, because, as with HIV, cells infected with the mycobacterium are killed by cytolysis, while antibody mediated therapies are often ineffective. Similarly, other infectious bacteria also intracellularly infect cells, such as chlamydia, rickettsial bacteria, staphylococci, treptocci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lymes disease bacteria are suitable targets for cell mediated therapies, and DC of the invention desirably present antigens from such bacteria and from cells infected by such bacteria.

Similarly, in a preferred embodiment, malarial antigens are presented by the DC of the invention. Malaria in humans is caused by four species of the parasite Plasmodium: *P. falciparum, P. vivax, P. knowlesi* and *P. malariae*. The major cause of malaria in humans is *P. falciparum* which infects 200 million to 400 million people every year, killing 1 to 4 million. Malaria is well studied, and a number of antigens suitable for cell mediated therapies are known.

In general, peptide loading for selected proteins and protein fragments onto dendritic cells is known in the art. In some embodiments it is preferable to facilitate uptake of whole proteins by the DC, which process and express peptide fragments of the protein on the surface of the DC. For example, Tsai et al., supra describe the loading of GP-100 tumor associated antigens onto DC. In other cases, it is desirable simply to wash endogenous peptide fragments off of the surface of DC (e.g., in a mildly acidic or detergent containing wash) and to then load peptide fragments onto the surface of the cell. Many such applications are known in the art.

Commonly, peptides are made synthetically or recombinantly. DC are pulsed with these peptides at a concentration of about 0.0010–100 μg/ml at a cell concentration of about 1×10$^6$ to 1×10$^7$ per ml, often in the presence of β$_2$-microglobulin for roughly 2–6 hours, e.g., at about 20° C.–37° C. In some cases, it is beneficial to use a cationic lipid-protein complex (e.g., using the cationic lipid DOTAP complexed to the protein of interest) to aid in uptake of proteins for processing and presentation by dendritic cells. See, e.g., Nair et al. *Int. J. Cancer* 70:706–715. Bedford (1997), supra describes peptide loading of Gag p24 onto antigen presenting cells. Mayordomo et al. (1995) *Nature Medicine* 1(12):1297–1291 describes loading and presentation of synthetic tumor peptides onto dendritic cells. Liu and Macpherson (1995) *Immunology* 84:241–246 describe processing of ovalbumin protein and presentation of ovalbumin peptides on the surface of dendritic cells for proliferation of T cells against ovalbumin (OVA). Similarly, Porgador and Gilboa (1995) *J. Exp. Med.* 182:255–260 describe loading of OVA onto dendritic cells and subsequent induction of a CTL response. A wide variety of variation on the above technique is possible, and known to those of skill in the art.

Carbohydrate antigens such as mucins are similarly loaded onto DCs of the invention. In some embodiments, the carbohydrate antigen is introduced into the DC as a moiety on a protein (e.g., as a carbohydrate side group), while in other embodiments, the carbohydrate antigen is washed onto the DC.

Idiotypic antibodies are also appropriate as antigens. Idiotypic antibodies are tumor antigens associated with a variety of conditions, and are suitable for presentation on the DC of the invention. For example, patients with non-Hodgkin's B-cell lymphoma who received an antitumor vaccine of idiotypic Ig protein showed humoral, proliferative and CTL immune responses. See, example 2 below; See also, Nelson et al. (1996) *Blood* 88(2):580–9. 16 non-Hodgkin's lymphoma patients immunized with autologous idiotypic ig molecules were monitored for changes in tumor-specific cytotoxic T-lymphocyte precursor (CTLp) frequency using limiting dilution analysis. Eleven patients had a significant increase ill tumor-specific CTLp. Eight of these 11 patients remained without evidence of disease or with stable minimal disease. In contrast, all five patients who did not have a significant change in tumor-specific CTLp developed progressive disease. Other autoimmune disorders such as Rheumatoid arthritis are also suitably treated by presenting idiotypic antibodies. See, e.g., Nelson et al. (1987) *J. Immunol* 138(5):1391–6. Finally, graft versus host and other transplantation rejection events are treated by loading appropriate peptides onto the DC of the invention.

Loading Dendritic Cells by Transduction with a Gene Encoding a Peptide of Interest It was recently shown that $CD34^+$ stem cells transduced with a gene for an antigen of interest can be differentiated into dendritic cells in vitro. See, Reeves et al. (1996) *Cancer Research* 56:5672–5677. Similarly, in the present invention, monocytes are transduced with a gene for an antigen of interest and expanded according to the methods herein, followed by differentiation into dendritic cells as described. One advantage of this approach is that multiple antigens from a single disease associated protein (MART-1, PSA, etc.) are expressed on the surface of the dendritic cell, providing for a broad range of cell mediated responses.

Additionally, Dendritic cells have very recently been successfully transduced with genes using retroviral and other vectors. See, Aicher et al. (1997) *Experimental Hematology* 25:39–44. Thus, in one embodiment, dendritic cells made by the methods of the invention are transduced with a retroviral vector having an expression cassette encoding an antigenic peptide such as a tumor antigen (TAA), viral antigen, or bacterial antigen (e.g., mycobacterial antigen). For example, recombinant expression cassettes are optionally placed into an MFG retroviral vector system, which is incubated in the presence of a DC cell. This procedure is described in Aicher et al., Id. and the references cited therein. Alternatively, naked DNA transfection of DC has provided enhanced immunogenicity against proteins encoded by the DC. See, Manickan et al. (1997) *Journal of Leukocyte Biology* 61:125–132. Accordingly, naked DNA techniques are also suitable. Also very recently, Brossart et al. (1997) *The Journal of Immunology* 3270–3276 described adenovirus mediated transfer of antigen to DC. Accordingly, adenovirus mediated delivery is used in on embodiment of the present invention. Additional suitable methods for transducing dendritic cells are described in Arthur et al. (1997) *Cancer Gene Therapy* 4:17–25. Poxvirus vectors using the adenovirus early promoter were found effective for dendritic cell transformation by Bronte et al. (1997) *PNAS* 94:3183–3188.

Several ways of transforming monocytes are applicable, including calcium phosphate precipitation, fusion of the recipient cells with bacterial protoplasts containing the DNA, treatment of the recipient cells with liposomes containing the DNA, DEAE dextran, receptor-mediated endocytosis, electroporation, micro-injection of the DNA directly into the cells, incubating viral vectors containing selected nucleic acids which encode polypeptides of interest with cells within the host range of the vector, calcium phosphate transfection, and many other techniques known to those of skill. See, e.g., *Methods in Enzymology*, vol. 185, Academic Press, Inc., San Diego, Calif. (D. V. Goeddel, ed.) (1990) or M. Krieger, *Gene Transfer and Expression—A Laboratory Manual*, Stockton Press, New York, N.Y., (1990) and the references cited therein, as well as Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3; and *Current Protocols in Molecular Biology*, F. M. Ausubel et al., eds., Current Protocols, a joint venture between Greene Publishing Associates, Inc. and John Wiley & Sons, Inc., (through the January 1997 Supplement) (Ausubel).

Several other approaches for introducing functional new genetic material into cells in vivo and ex vivo have also been used, and are applicable. These include liposome based gene delivery (Debs and Zhu (1993) WO 93/24640; Mannino and Gould-Fogerite (1988) *Biotechniques* 6(7): 682–691; Rose U.S. Pat No. 5,279,833; Brigham (1991) WO 91/06309; and Feigner et al. (1987) *Proc. Natl. Acad. Sci. USA* 84: 7413–7414) and replication-defective retroviral vectors harboring a therapeutic polynucleotide sequence as part of the retroviral genome (see, e.g., Miller et al. (1990) *Mol. Cell. Biol*. 10.4239 (1990); Kolberg (1992) *J. NIH Res*. 4:43, and Cornetta et al. *Hum. Gene Ther*. 2:215 (1991)). Widely used retroviral vectors include those based upon murine leukemia virus (MuLV), gibbon ape leukemia virus (GaLV), ecotropic retroviruses, simian immuno deficiency virus (SIV), human immuno deficiency virus (HIV), and combinations thereof. See, e.g., Buchscher et al. (1992) *J. Virol*. 66(5) 2731–2739; Johann et al. (1992) *J. Virol*. 66 (5):1635–1640 (1992); Sommerfelt et al., (1990) *Virol*. 176:58–59; Wilson et al. (1989) *J. Virol*. 63:2374–2378; Miller et al., *J. Virol*. 65:2220–2224 (1991), and Rosenburg and Fauci (1993) in *Fundamental Immunology, Third Edition* Paul (ed) Raven Press, Ltd., New York and the references therein, and Yu et al., *Gene Therapy* (1994) supra).

Many recombinant expression cassettes comprising a gene encoding a protein or peptide of interest suitable for transformation, or for recombinant expression of the peptide (e.g., in a standard bacterial or yeast expression system), are known to persons of skill. These can be made using standard recombinant or synthetic techniques, and one of skill can construct a variety of clones containing functionally equivalent nucleic acids, such as nucleic acids which encode the same polypeptide. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Sambrook, Ausubel and Berger, supra. The nucleic acid compositions of this invention, whether RNA, DNA, cDNA, genomic DNA, or a hybrid of the various combinations, are isolated from biological sources or synthesized in vitro. The nucleic acids of the invention are present in transduced or transfected cells, in transduced or transfected cell lysates, or in a partially purified or substantially pure form.

In vitro amplification techniques suitable for amplifying sequences to be subcloned into an expression vector are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook and Ausubel, as well as Mullis et al., (1987) U.S. Pat. No. 4,683,202; PCR *Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science 241, 1077–1080*; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564.

Nucleic acid synthesis techniques are available, such as the solid phase phosphoramidite triester method described by Beaucage and Caruthers (1981), *Tetrahedron Letts.*, 22(20):1859–1862, e.g., using an automated synthesizer, e.g., as described in Needham-VanDevanter et al. (1984) *Nucleic Acids Res.*, 12:6159–6168. Nucleic acids can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

One of skill will recognize many ways of generating alterations in a given nucleic acid sequence such as a known cancer marker. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97; Roberts et al. (1987) *Nature* 328:731–734 and Sambrook et al. (1989) *Molecular Cloning—A Laboratory Manual* (2 nd Ed) Vol. 1–3; Innis, Ausbel, Berger, Needham VanDevanter and Mullis (all supra).

In addition to recombinant expression, polypeptides to be loaded onto DC can be synthetically prepared in a wide variety of well-known ways. Polypeptides of relatively short size are typically synthesized in solution or on a solid support in accordance with conventional techniques. See, e.g., Merrifield (1963) *J. Am. Chem. Soc.* 85:2149–2154. Various automatic synthesizers and sequencers are commercially available and can be used in accordance with known protocols. See, e.g., Stewart and Young (1984) *Solid Phase Peptide Synthesis*, 2d. ed., Pierce Chemical Co. Polypeptides are also produced by recombinant expression of a nucleic acid encoding the polypeptide followed by purification using standard techniques. See also, Manickan et al., supra.

Expression cassettes used to transform cells preferably contain DNA sequences to initiate transcription and sequences to control the translation of any encoded antigenic protein or peptide sequence. These sequences are referred to as expression control sequences. When illustrative expression control sequences active in mammalian cells are obtained from the SV-40 promoter (*Science*, 222:524–527, 1983), the CMV I.E. Promoter (*Proc. Natl. Acad. Sci.* 81:659–663, 1984) and the metallothionein promoter (*Nature* 296:39–42, 1982). Pol III promoters such as $tRNA_{val}$, a house-keeping cellular gene promoter, and the adenovirus VA1, a strong viral promoter are also desirable. The cloning vector containing the expression control sequences is cleaved using restriction enzymes and adjusted in size as necessary or desirable and ligated with nucleic acid coding for the target polypeptides by means well known in the art.

Polyadenlyation or transcription terminator sequences from known mammalian genes are typically incorporated into the vector. Poll III termination sequences are outlined in Geiduschek, E. P., *Ann. Rev. Biochem.* 57:873–914 (1988). An example of a terminator sequence is the polyadenlyation sequence from the bovine growth hormone gene. Sequences for accurate splicing of the transcript are also be included. An example of a splicing sequence is the VP1 intron from SV40 (Sprague, J. et al., 1983, *J. Virol.* 45: 773–781).

Additionally, sequences to control replication in the host cell is optionally incorporated into the vector such as those found in bovine papilloma virus type-vectors. Saveria-Campo, M., 1985, "Bovine Papilloma virus DNA a Eukaryotic Cloning Vector" in *DNA Cloning Vol. II a Practical Approach Ed.* D. M. Glover, IRL Press, Arlington, Va. pp. 213–238.

Where a retroviral packaging vector is used, a packaging site containing the nucleic acids responsible for packaging viral RNA into the retroviral particle is included with the expression cassette. Typically, this includes nucleic acids corresponding to those from a retrovirus located between the LTR of the retrovirus and the gag initiation codon.

Isolation of and expansion of T cells

T cells are isolated from mammals in some embodiments of the invention where the T cell is activated in vitro by contact with a dendritic cell of the invention. Several techniques for T cell isolation are known. The expression of surface markers facilitates identification and purification of T cells. Methods of identification and isolation of T cells include FACS, incubation in flasks with fixed antibodies which bind the particular cell type and panning with magnetic beads.

In one method, Ficoll-Hypaque density gradient centrifugation is used to separate PBMC from red blood cells and neutrophils according to established procedures. Cells are washed with modified AIM-V (which consists or AIM-V (GIBCO) with 2 mM glutamine, 10 µg/ml gentamicin sulfate, 50 µg/ml streptomycin) supplemented with 1% fetal bovine serum (FBS). Enrichment for T cells is performed by negative or positive selection with appropriate monoclonal antibodies coupled to columns or magnetic beads according to standard techniques. An aliquot of cells is analyzed for cell surface phenotype including CD4, CD8, CD3 and CD14.

Cells are washed and resuspended at a concentration of $5 \times 10^5$ cells per ml of AIM-V modified as above and containing 5% FBS and 100 U/ml recombinant IL-2 (rIL-2) (supplemented AIM-V). Where the cells are isolated from and HIV$^+$ patient, 25 nM CD4-PE40 (a recombinant protein consisting of the HIV-1-binding CD4 domain linked to the translocation and ADP-ribosylation domains of *Pseudomonas aeruginosa* exotoxin A), or other similar recombinant cytotoxic molecule which selectively hybridizes to HIV is added to the cell cultures for the remainder of the cell expansion to selectively remove HIV infected cells from the culture. CD4-PE40 has been shown to inhibit p24 production in HIV-1-infected cell cultures and to selectively kill HIV-1-infected cells.

To stimulate proliferation, OKT3 monoclonal antibody (Ortho Diagnostics) is added to a concentration of 10 ng/ml and the cells are plated in 24 well plates with 0.5 ml per well. The cells are cultured at 37° C. in a humidified incubator with 5% $CO_2$ for 48 hours. Media is aspirated from the cells and 1 ml of vector-containing supernatant (described below) supplemented with 5 μl/ml of protamine sulfate, 100 U/ml rIL-2, 100 U/ml penicillin, 0.25 μg/ml amphotericin B/ml and an additional 100 μg/ml streptomycin (25 nM CD4-PE40 can be added as described above).

Isolating Cells With Selectable Markers

A variety of cells are used in the methods of the invention, including monocytes, T cells and dendritic cells. Each of these cell types is characterized by expression of particular markers on the surface of the cell, and lack of expression of other markers. For instance, in the mouse, some (but not all) dendritic cells express 33D1 (DC from spleen and Peyer's patch, but not skin or thymic medulla), NLDC145 (DC in skin and T-dependent regions of several lymphoid organs and CD11c (CD11c also reacts with macrophage). T cells are positive for various markers depending on the particular subtype, most notably CD4 and CD8.

The expression of surface markers facilitates identification and purification of these cells. These methods of identification and isolation include FACS, column chromatography, panning with magnetic beads, western blots, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioinmmunoassays (RIAs), enzyme-linked immunosorbent assays (ELISAs), immunofluorescent assays, and the like. For a review of immunological and immunoassay procedures in general, see Stites and Terr (eds.) 1991 *Basic and Clinical Immunology* (7th ed.) and Paul supra. For a discussion of how to make antibodies to selected antigens see, e.g. Coligan (1991) Current Protocols in Immunology Wiley/Greene, N.Y.; and Harlow and Lane (1989) *Antibodies: A Laboratory Manual* Cold Spring Harbor Press, N.Y.; Stites et al. (eds.) Basic and Clinical Immunology (4th ed.)

Cell isolation or immunoassays for detection of cells during cell purification can be performed in any of several configurations, e.g., those reviewed in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B. V., Amsterdam; Harlow and Lane, supra; Chan (ed.) (1987) *Immunoassay: A Practical Guide Academic* Press, Orlando, Fla.; Price and Newman (eds.) (1991) *Principles and Practice of Immunoassays* Stockton Press, N.Y.; and Ngo (ed.) (1988) *Non-isotopic Immunoassays* Plenum Press, N.Y.

Most preferably, cells are isolated and characterized by flow cytometry methods such a FACS analysis. A wide variety of flow-cytometry methods are known. For a general overview of fluorescence activated flow cytometry see, for example, Abbas et al. (1991) *Cellular and Molecular immunology* W. B. Saunders Company, particularly chapter 3, and Kuby (1992) *Immunology* W. H. Freeman and Company, particularly chapter 6. FACS machines are available, e.g., from Becton Dickinson.

Labeling agents which can be used to label cell antigen include e.g., monoclonal antibodies, a polyclonal antibodies, proteins, or other polymers such as affinity matrices, carbohydrates or lipids. Detection proceeds by any known method, such as immunoblotting, western blot analysis, tracking of radioactive or bioluminescent markers, capillary electrophoresis, or other methods which track a molecule based upon size, charge or affinity. The particular label or detectable group used and the particular assay are not critical aspects of the invention. The detectable moiety can be any material having a detectable physical or chemical property. Such detectable labels have been well-developed in the field of gels, columns, solid substrates cell cytometry and immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., LacZ, CAT, horse radish peroxidase, alkaline phosphatase and others, commonly used as detectable enzymes, either as marker gene products or in an ELISA), nucleic acid intercalators (e.g., ethidium bromide) and colorimetric labels such as colloidal gold or colored glass or plastic (e.g. polystyrene, polypropylene, latex, etc.) beads.

The label is coupled directly or indirectly to the desired component of the assay according to methods well known in the art. As indicated above, a wide variety of labels are used, with the choice of label depending on the sensitivity required, ease of conjugation of the compound, stability requirements, available instrumentation, and disposal provisions. Non radioactive labels are often attached by indirect means. Generally, a ligand molecule (e.g., biotin) is covalently bound to a polymer. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled, anti-ligands. Alternatively, any haptenic or antigenic compound can be used in combination with an antibody.

Labels can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labelling or signal producing systems which are used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it is optionally detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels are detected by providing appropriate substrates for the enzyme and detecting the resulting reaction product.

Finally, simple colorimetric labels are often detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of antibodies. In this case, cells are agglutinated by samples comprising the antibodies bound to the cells. In this format, none of the components need be labeled and the presence of the target antibody is detected by simple visual inspection.

Depending upon the assay, various components, including the antibody, or anti-antibody, are typically bound to a solid surface. For instance, in one preferred embodiment, unwanted cells are panned out of cell culture using appropriate antibodies bound to a substrate over which the cells are passed. Many methods for immobilizing biomolecules to a variety of solid surfaces are known in the art. For instance, the solid surface is optionally a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, a flask, or a glass, silica, plastic, metallic or polymer bead. The desired component is optionally covalently bound, or noncovalently attached through nonspecific bonding. A wide variety of organic and inorganic polymers, both natural and synthetic are optionally employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which are appropriate depending on the assay include paper, glasses, ceramics, metals, metalloids, semiconductive materials, cements and the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable.

Diagnostic Assays

In one embodiment, diagnostic assays are provided. These assays are used to determine whether a cell population (e.g., a blood or cell sample from a patient) express a selected antigen. In the assays, isolated dendritic cells expressing the selected antigen are used to activate T-cells against the antigen. The cell population is then exposed to the activated T-cells, and lysis of the cells is monitored (e.g., by 51Cr release, trypan blue exclusion, or presence of cytoplasmic enzymes such as lactose dehydrogenase). If the observed lysis is higher than an appropriate control, the population of cells comprises the antigen. This can be used, e.g., to assess whether tumor cells (or infected cells) express a particular antigen. If the tumor is found to express a particular antigen, a clinician can use the information to better select therapeutics against the tumor. Similar considerations apply for infected cells (virally, bacterially or parasitically).

These diagnostic assays can be used in conjunction with the therapeutic aspects of the invention, i.e., a tumor sample can be screened against a panel of activated T-cells to determine which activated T-cells or recombinant DCs can be used to immunize against the tumor.

Immunizations can also be monitored with DCs. Precursor frequency and/or T-cell reactivity is monitored by exposure to recombinant DCs, e.g., using DCs corresponding to the DCs which were used for immunization or to stimulate T-cells.

MLR Assays

In order to determine the antigen presenting cell activity of antigen presenting cells such as DC, the proliferative effect of these antigen presenting cells on T cells is tested in an MLR assay. MLR assays or "mixed lymphocyte response" assays are the standard in vitro assay of antigen presenting function in cellular immunity. The assay measures the proliferation of T cells after stimulation by a selected cell type. The number of T cells produced are typically characterized by measuring T cell proliferation based on incorporation of $^3$H-thymidine in culture. Similar methods are used in vivo in nude or SCID mouse models. See also, Paul (supra) at chapter 31; Takamizawa et al. (1997) *Journal of Immunology* 2134–2142; Uren and Boyle (1989) *Transplant Proc.* 21:208; Uren and Boyle (1989) *Transplant Proc.* 21:3753; Bedford et al. (1997) *Journal of Acquired Immune Deficiency Syndromes and Human Retrovirology* 14:301–306; Zhou and Tedder (1996) *PNAS* 93:2588–2592. Mehta-Damani et al. (1995) *Eur J. Immunol* 25:1206–1211 describe the generation of antigen specific T cells from naive precursors by APC presentation of keyhole limpet hemocyanin (KLH), sperm whale myoglobin (SWM) and HIV gp160, and MLR assays for the detection of T cell proliferation. Additional MLR assays are described in Egner et al. (1993) *Journal of Immunology* 150:3043–3053.

Figure 2:
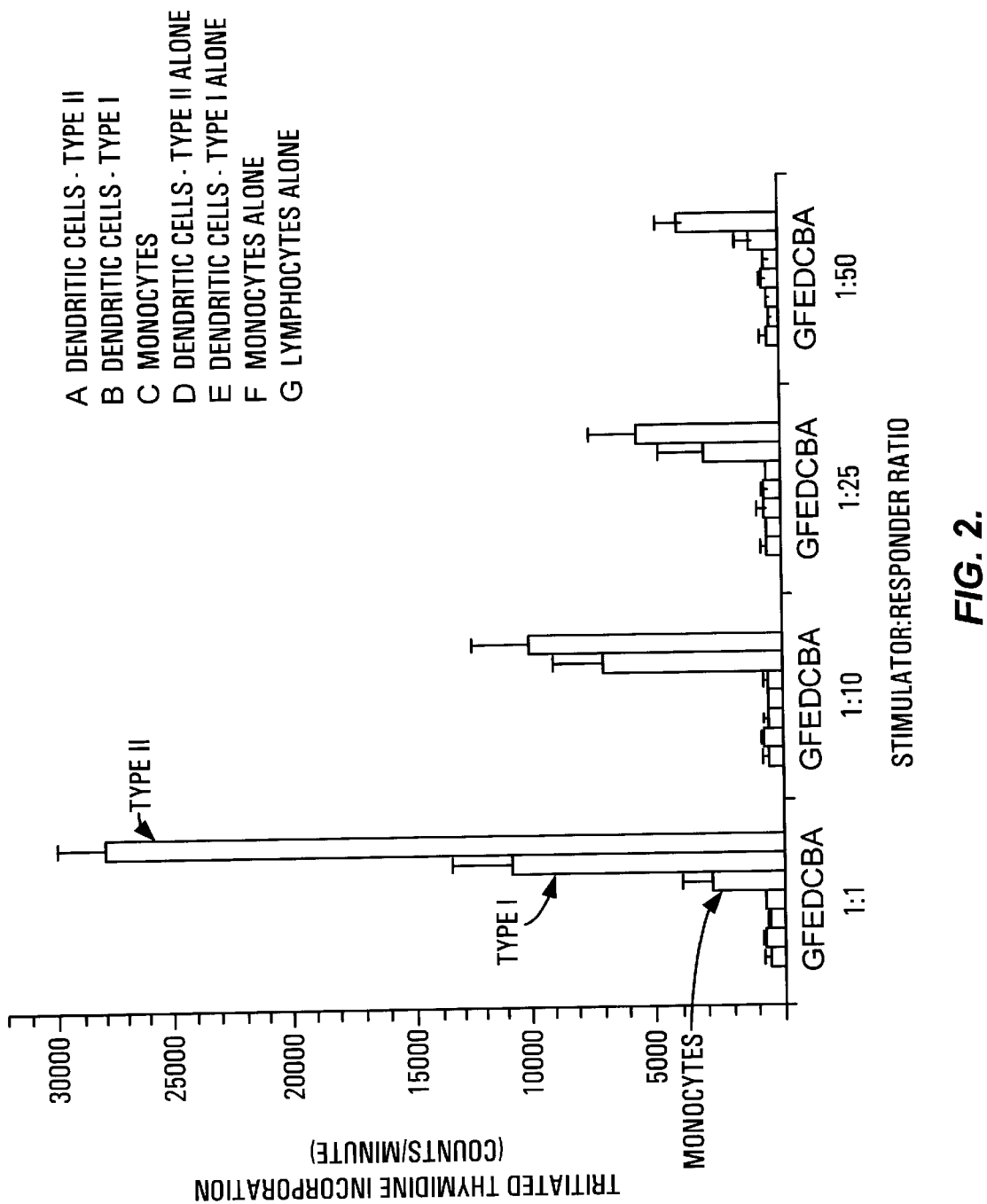
FIG. 2 is a graph of type I versus type II dendritic cell activity in mixed lymphocyte reactions.

In one example of an MLR, suspensions of responder T cells were cultured with allogeneic stimulator cells. When the activating stimulus was a foreign MHC on the allogenic stimulator, responders do not need to be primed. Simulators are irradiated to prevent uptake of $^3$H thymidine. Simulators and responders are mixed in selected ratios (i.e., 1:1, 1:10, 1:25 & 1:50) and plated in 96 well plates. The cells are cultured together for 5 days, pulsed with thymidine for 18 hours and harvested. FIG. 2 shows a graph of Type I (baseline) versus Type II (activated) dendritic cell activity in allogenic MLR. See also, Examples 1–3.

CTL Response Assay

A cytotoxic T lymphocyte response is a cell-mediated immune response in which a CTL causes cell death of a target cell. CTL responses are typically measured by monitoring lysis of target cells by CTLs. An immunogenic peptide or antigenic peptide is a peptide which forms all or a part of an epitope recognized by a T cell (e.g., an epitope which is recognized optionally further includes an MHC moiety), and which is capable of inducing a cell mediated response (including a T helper response). Proteins are processed in antigen presenting cells into antigenic peptides and expressed, e.g., on MHC receptors (or in the context of other molecules such as cell surface proteins) on the surface of antigen presenting cells. Thus, some antigenic peptides are capable of binding to an appropriate MHC molecule on a target cell and inducing a cytotoxic T cell response, e.g., cell lysis or specific cytokine release against the target cell which binds the antigen, or other T helper response. Immunogenic compositions optionally include adjuvants, buffers, and the like.

In one example of a CTL assay, lymphocytes (effector cells) are removed from an immunized animal (or human) and tested for their ability to lyse target cells. frequently, the target cells are engineered to express one or more of the epitopes contained in the immunogen (e.g., a viral antigen, or a cancer antigen as described, supra.). The target and effector cells are from the same immunohistocompatibility group, i.e., they have the same MHC components on their surfaces. The lymphocytes from the immunized animal (effector cells) are incubated with the target cells. After approximately four hours, the mixed cultures are assayed for lysis of the target cells. Lysis is typically measured by the release of $^{51}$Cr that had previously been taken up by the cells, or by the release of cytoplasmic proteins such as lactose dehydrogenase. Boehringer Mannheim (Indianapolis, Ind.) makes a kit (catalogue number 1644793) suitable for measuring lactose dehydrogenase release. An example of a target cell is a cell transduced with a viral vector encoding a target protein, e.g., a recombinant vaccinia virus vector encoding Gag or Env to test effector cell activity for effectors from animals immunized with a Gag-Env pseudovirion. An example CTL assay is found in Manickan (1997), supra.

Ex Vivo Therapy

Ex vivo therapeutic methods for making transduced dendritic cells and activated T cells are provided. In the methods, dendritic cells are transduced in vitro. These transduced dendritic cells are used to activate T cells in vitro, or the dendritic cells are introduced into a mammal to activate the T cell in vivo. T cells such as $CD8^+$ CTLs activated in vitro are introduced into a mammal where they are cytotoxic against target cells bearing antigenic peptides corresponding to those the T cells are activated to recognize on class I MHC molecules. These target cells are typically cancer cells, or infected cells which express unique antigenic peptides on their MHC class I surfaces. It was demonstrated that dendritic cells expressing cancer antigens activate T-cells against corresponding cancer cells.

Similarly, helper T-cells (e.g., $CD4^+$ T cells), which recognize antigenic peptides in the context of MHC class II, are also stimulated by the recombinant DCs, which comprise antigenic peptides both in the context of class I and class II MHC. These helper T-cells also stimulate an immune response against a target cell. As with cytotoxic T-cells, helper T-cells are stimulated with the recombinant DCs in vitro or in vivo.

The dendritic cells and T cells are preferably isolated from the same mammal into which the activated T cells are to be active ("autologous" therapy). Alternatively, the cells can be those from a donor or stored in a cell bank (e.g., a blood bank).

Thus, a patient infected with a virus such as HIV-1 or suffering from a cancer such as a melanoma can be treated by administering recombinant dendritic cells, or by using recombinant dendritic cells to activate a population of the patient's T cells against the infection or cancer, and introducing the T cells back into the patient as described herein. Thus, the present invention provides a method of producing cytotoxic T cells in vitro, ex vivo or in vivo. In addition, DC are administered for activation of T cells in vivo. Furthermore, DC have therapeutic benefits beyond simple antigen presentation. For example, DC release IL-12, which can have proliferative effects on T cells.

In Vivo Therapy

T cells or dendritic cells can be administered directly to the organism to produce T cells active against a selected cancerous or infected cell type. Administration of these is by any of the routes normally used for introducing a cell into ultimate contact with a mammal's blood or tissue cells.

The cells are administered in any suitable manner, often with pharmaceutically acceptable carriers. Suitable methods of administering cells in the context of the present invention to a patient are available, and, although more than one route can be used to administer a particular cell composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention. Most typically, quality controls (microbiology, clonogenic assays, viability tests), are performed and the cells are reinfused back to the patient. See, for example, Korbling, M. et al. (1986) *Blood*, 67:529–532 and Haas et al. (1990) *Exp. Hematol.* 18:94–98.

Formulations suitable for parenteral administration, such as, for example, by intraarticular (in the joints), intravenous, intramuscular, intradermal, intraperitoneal, and subcutaneous routes, and carriers include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Intravenous, subcutaneous and intraperitoneal administration are the preferred method of administration for dendritic or T cells of the invention.

The dose of cells (e.g., activated T cells, or dendritic cells) administered to a patient, in the context of the present invention should be sufficient to effect a beneficial therapeutic response in the patient over time, or to inhibit growth of cancer cells, or to inhibit infection. Thus, cells are administered to a patient in an amount sufficient to elicit an effective cell mediated response to a virus or tumor, or infected cell, and/or to alleviate, reduce, cure or at least partially arrest symptoms and/or complications from the particular disease or infection. An amount adequate to accomplish this is defined as a "therapeutically effective dose." The dose will be determined by the activity of the T cell or dendritic cell produced and the condition of the patient, as well as the body weight or surface area of the patient to be treated. The size of the dose also will be determined by the existence, nature, and extent of any adverse side-effects that accompany the administration of a particular cell in a particular patient. In determining the effective amount of the cell to be administered in the treatment or prophylaxis of diseases such as AIDS or cancer (e.g., metastatic melanoma, prostate cancer, etc.), the physician needs to evaluate circulating plasma levels, CTL or helper toxicity, progression of the disease, and the production of immune response against any introduced cell type.

Prior to infusion, blood samples are obtained and saved for analysis. Generally at least about $10^4$ to $10^6$ and typically, between $1 \times 10^8$ and $1 \times 10^{10}$ cells are infused intravenously or intraperitoneally into a 70 kg patient over roughly 60–120 minutes. Intravenous infusion is preferred. Vital signs and oxygen saturation by pulse oximetry are closely monitored. Blood samples are obtained 5 minutes and 1 hour following infusion and saved for analysis. Cell reinfusion are repeated roughly every month for a total of 10–12 treatments in a one year period. After the first treatment, infusions can be performed on a outpatient basis at the discretion of the clinician. If the reinfusion is given as an outpatient, the participant is monitored for at least 4 hours following the therapy.

For administration, cells of the present invention (DC or activated T cells) can be administered at a rate determined by the LD-50 (or other measure of toxicity) of the cell type, and the side-effects of the cell type at various concentrations, as applied to the mass and overall health of the patient. Administration can be accomplished via single or divided doses. The cells of this invention can supplement other treatments for a condition by known conventional therapy, including cytotoxic agents, nucleotide analogues and biologic response modifiers. Similarly, biological response modifiers are optionally added for treatment by the DCs or activated T cells of the invention. For example, the cells are optionally administered with an adjuvant, or cytokine such as GM-CSF, IL-12 or IL-2. Doses will often be in the range of $1\times10^5$ to $1\times10^7$ cells per administration.

Tumor antigen genes are expressed by dendritic cells using retroviral transduction, and these dendritic cells (and T cells activated by the dendritic cells) can be used as anti-tumor therapeutics. Transduced dendritic cells are valuable reagents for active immunization strategies against cancer and infectious diseases, and are useful in vitro to uncover unique tumor epitopes and antigens, and as a tool to study the basic biology of primary dendritic cells. Accordingly, in one specific example of the administration methods shown above, metastatic melanoma patients are immunized with autologous dendritic cells transduced with the MART-1 or GP100 tumor antigen genes to inhibit melanoma metastasis and disease progression, or, alternatively, melanoma patients are immunized with activated T cells (or both activated T-cells and dendritic cells) transduced with the MART-1 or GP100 tumor antigen genes to inhibit melanoma metastasis and disease progression, using the dosing and administration methods set forth above. In another specific example, patients with non-Hodgkin's B-cell lymphoma are immunized with DCs expressing autologous idiotypic Ig molecules, or with T-cells activated ex vivo by such DCs. See also, Example 3.

In Vitro Assays And Kits

The present invention provides commercially valuable assays and kits to practice the assays. In the assays of the invention, dendritic cells are transduced or otherwise caused to present a putative T cell MHC class I associated antigen. The dendritic cell is used to activate the T cell, which is then tested for cytotoxic activity against a class of target cells thought to comprise the putative antigen. Cytotoxicity indicates that the target cells comprise the antigen, and that the antigen is sufficient to mediate a T cell recognition of the target cell. This assay provides investigators with a lead molecule for use in gene therapy or vaccination therapies. Because the transduced dendritic cells can be established in culture, or made in batches, several potential target cell populations can be screened. Thus, libraries of potential tumor antigens can be screened by cloning into dendritic cells. The ability to screen and identify tumor antigens is of considerable commercial value to pharmaceutical and other drug discovery companies.

Kits based on the assay are also provided. The kits typically include a container, and monocytes or dendritic cells. The kits optionally comprise directions for performing the assays, cell transformation vectors, cytokines, or instructions in the use of any of these components, or the like.

In a further aspect, the present invention provides for the use of any composition, cell, cell culture, apparatus, apparatus component or kit herein, for the practice of any method or assay herein, and/or for the use of any apparatus or kit to practice any assay or method herein and/or for the use of cells, cell cultures, compositions or other features herein as a medicament. The manufacture of all components herein as medicaments for the treatments described herein is also provided.

EXAMPLES

The following examples are provided by way of illustration only and not by way of limitation. Those of skill will readily recognize a variety of noncritical parameters which can be changed or modified to yield essentially similar results.

Example 1

Expansion of Monocytes and Differentiation into Dendritic Cells

The emerging use of vaccines for the treatment of cancer by attempting to make the immune system work better, is relatively new. In order for the immune system to recognize and eliminate tumors, antigen (Ag) from the tumor must be presented to the immune system. Dendritic cells (DC) are the most potent antigen presenting cells (APC) known in the immune system. In vivo, dendritic cells are a heterogeneous population of cells distributed in very low numbers in most tissues and until recently were not able to be grown in culture. This lack of adequate numbers of cells to study has made their characterization difficult. It is believed that they are of myeloid origin although the differentiation pathway(s) is/are still unclear. The presence of molecules or markers on the surface of cells can be detected by antibodies directed against these markers and used to establish a cell's phenotype, thereby allowing us to classify cells of the immune system. However, to date, unique cell surface marker(s) have not been identified for dendritic cells. Thus, DC are characterized by their morphology, their pattern of expression of a group of cell surface markers, and functional assays. They stain negative for CD3, CD4, CD8, CD14, CD16, CD19, and CD56. They express high levels of CD1a, the integrins CD11a & CD11b, CD40, MHC class I & class 11, and the costimulatory molecules CD80 (B7-1) & CD86 (B7-2).

It has been shown that dendritic cells can differentiate from CD34 positive progenitor cells (bone marrow stem cells) stimulated by granulocyte/macrophage-colony stimulating factor (GM-CSF) and tumor necrosis factor (TNF-α) or from monocytes by culturing with GM-CSF and Interieukin 4 (IL-4). In this example, we used elutriation (counter now centrifugal separation) to obtain large numbers of >90% pure monocytes ($4-6\times10^8$) from apharesed peripheral blood leukocytes to generate 1 DCs. Two different types of dendritic cells, baseline (Type I) and activated (Type II), characterized by morphology, phenotype, and functional assays were obtained when the monocytes were cultured with various combinations of GM-CSF, IL4, and TNF-α. Greater than $5\times10^7$ autologous dendritic cells of either phenotype were generated. Furthermore, the data indicates that monocytes can differentiate into both types of DC depending on the cytokine environment and that this differentiation is not terminal. MONOCYTE SELECTION: Apheresed peripheral blood leukocytes from normal human donors were processed over Ficoll gradients, harvested and washed. Peripheral blood leukocytes were separated by elutriation (counter flow centrifugal separation) into distinct cell pools; platelets, lymphocytes, and monocytes. Briefly, the peripheral blood mononuclear cells (PBMC) are injected into, the JE-5.0 Elutriation System (Beckman Instruments, Inc. Palo Alto, Calif.) and 50 ml. cell fractions were collected. Cell size distribution of each fraction was determined by electronically measuring electrical impedance on the Coulter Multisizer (Coulter Electronics Limited, Miami Fla.). Analyzed fractions of >90% pure monocytes were pooled and washed. MONOCYTE PROLIFERATION CULTURE CONDITIONS USING IL-3. Monocytes were cultured at $1\times10^6$ cells/ml in RPMI 1640 (BioWhittaker, Walkersville, Md.) supplemented with L-glutamine (2 mM), sodium pyruvate (1 mM), non-essential amino acids (0.1 mM), penicillin (50 units/ml), streptomycin (50 ug/ml), BME (50 mM) and 10% fetal calf serum. IL-3 (10 ng/ml) was added at day 0 and the cells were cultured for 5–7 days to obtain proliferating monocytes. At the end of the 5–7 day culture period, the IL-3 was removed from the culture by pelleting the cells and removing the supernatant, then washing the cell pellet once more with phosphate buffered saline (PBS). The washed cells were then placed in culture with GM-CSF and IL-4 as indicated below. DENDRITIC CELL CULTURE CONDITIONS: Monocytes were cultured at $1\times10^6$ cells/ml in RPMI 1640 (BioWhittaker, Walkersville, Md.) supplemented with L-glutamine (2 mM), sodium pyruvate (1 mM), non-essential amino acids (0.1 mM), penicillin (50 units/mi), streptomycin (50 ug/m]), BME (50 mm) and 10% fetal calf serum. GM-CSF (100 u/ml) and IL-4 (50 ng/ml) were added at day 0 and the cells were cultured for 10–12 days to obtain Type I (baseline) DC; TNF-α (20 ng/ml) was added to aliquots of Type I (baseline) cultures at 10–12 days for 48 hours to obtain Type II DC. Cultures were fed every 6–7 days by removing ½ of the culture volume and adding an equal volume of fresh media containing GM-CSF and IL-4 for the entire culture volume. FACS ANALYSIS: Cells were incubated for 15 min. at 40C in PBS, 2% bovine serum albumin & 0.1% sodium azide with FITC- or PE-conjugated mAb CD3, CD4, CD8, CD11b, CD14, CD19, CD56, HLA DR, CD80 (Becton Dickinson, San Jose, Calif.), CD1a, CD32, CD86, Pan MHC Class I (PharMingen, San Diego, Calif.), CD16 (20 ul of 1:100 3GS, Medarex, Annandale, N.J.), CD33 (AMAC, Inc., Westrook, Me.), or CD83 (20 ul of 1:500 HB15, available from ImmunoTech (a Coulter Company), Westbrook, Me.). After washing, cells were resuspended in 1% paraformaidehyde and analyzed on the Epics Profile Analyzer (Coulter Cytometry, Miami, Fla.). For CD83 labeling, after incubating with CD83 and washing, cells were incubated for 15 min. at 40 C with 20 ul of 1:20 goat F(ab')2 FITC-labeled anti-mouse IgG (Boehringer Mannheim Biochemicals, Indianapolis, Ind.). An alternate FACS analysis method is provided in Example 2.

Figure 4:
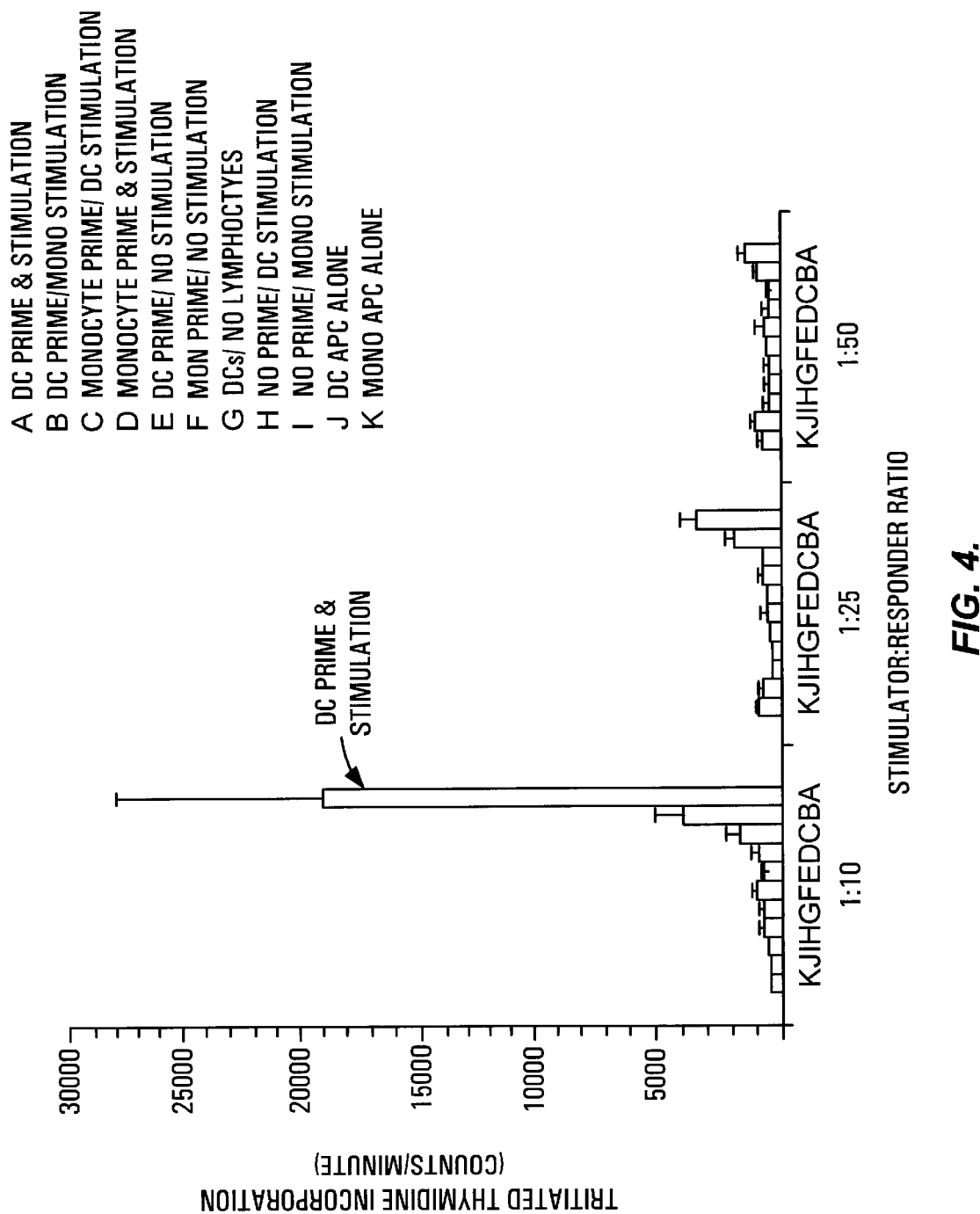
FIG. 4 is a graph showing the results of a naive antigen presentation with 10 micrograms of KLH.

The phenotype of in vitro derived dendritic cells as measured by FACS analysis is shown in Table 1.

calls were mixed with different numbers of washed, KLH pulsed, stimulator DC or MO. Cells were cultured together for 10 days. These "primed" T cells @$1\times10^5$ cells/well were then restimulated with a second set of KLH pulsed, washed, irradiated, autologous DC or MO, and cultured together for 5 days. After 5 days of culture, cells were pulsed for 18 hours with $^3$H thymidine, harvested, and measured as described above. The results are shown in FIG. 4. FACS: The DC's were negative for CD14, had moderate levels of the costimulatory molecules CD80 (B7-1,) & CD86 (87-2), and high expression of CD1a and MHC class I & class II. When TNFα was added to Type I (baseline) dendritic cells, CD1a was downregulated, while CD80, CD83 & C086 were increased in their expression in a dose responsive maner, giving rise to Type II DC. MLR: Type II DC stimulated allogeneic responding T cells at all stimulator to responder ratios. Type I (baseline) DC also had stimulatory capacity at all ratios but to a lesser extent. Monocytes, however, were only able to stimulate the responding T cells when they were mixed at the highest ratio of 1:1. Their activity falls off dramatically (down to background) at the next lower ratio tested. NAIVE ANTIGEN PRESENTATION: GM-CSF & IL4 cultured dendritic cells (Type 1) performed very well in this assay. All monocytes and dendritic cells used in this system were antigen pulsed with the naive antigen KLH. Autologous responding T cells "primed" with DC and "stimulated" with DC gave the highest response to KLH and maintained activity into the highest stimulator to responder ratio. As demonstrated, MO were much less potent simulators of primed T cells than dendritic cells. This was shown when T cells were primed with DC and then stimulated with monocytes in that the resulting T cell activity was present, but much lower. T lymphocytes primed with MO, however, FACS Profile of In-Vitro Derived Dendritic Cells

| GM-CSF @ 100 U/m, IL-4 @ 50 ng/ml (100 U) | CD1a | CD3 | CD4 | CD8 | CD11b | CD14 | CD16 | CD19 | CD32 | CD33 | CD56 | CD80 | CD83 | CD86 | MHC 1 | HLA-DR |
|---|---|---|---|---|---|---|---|---|---|---|---|---|---|---|---|---|
| DC | +(67) | − | − | − | +(100) | − | − | − | + | + | − | +(28) | − | +(52) | + | + |
| DC, TNF α 0.05 ng/ml | +(56) | − | − | − | +(100) | − | − | − | + | + | − | +(57) | +/−(7) | +(65) | + | + |
| DC, TNF α 5 ng/ml | +(29) | − | − | − | +(100) | − | − | − | + | + | − | +(81) | +(30) | +(96) | + | + |
| DC, TNF α 20 ng/ml | +(16) | − | − | − | +(100) | − | − | − | + | + | − | +(83) | +(65) | +(99) | + | + |
| Monocytes | +(16) | − | + | − | +(75) | +(90) | − | − | + | + | − | +(29) | − | +(79) | + | + |

Where +(X) = % of cells clearly positive for specified marker.

Figure 3:
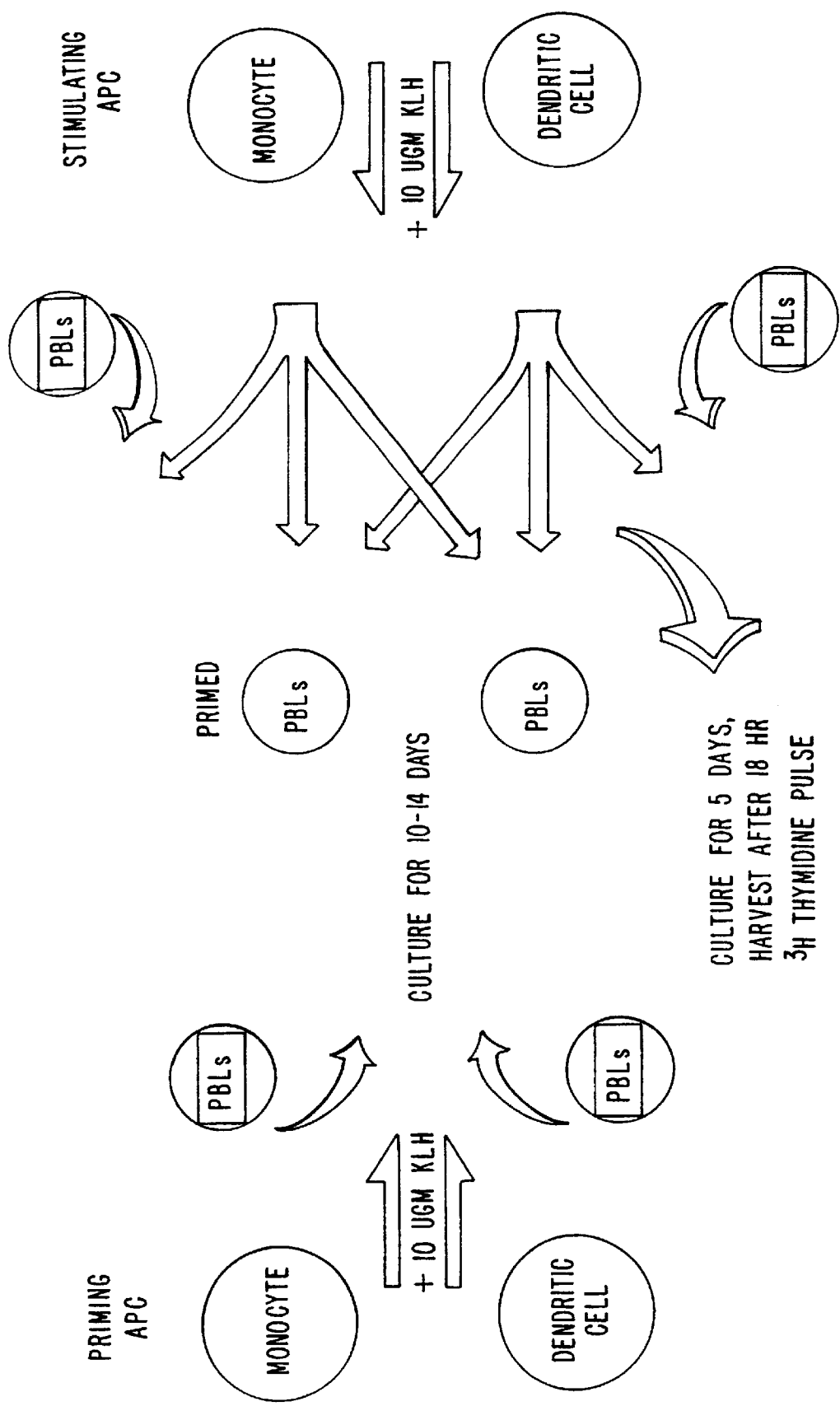
FIG. 3 is shows a naive antigen presentation experiment.

MLR: Allogeneic responding T cells from normal donors were cultured @$1.0\times10^5$ cells/well in 96 well flat-bottom microplates (Costar Corp., Cambridge, Mass.) with different numbers of irradiated (3000 rad from a 137Cs source) stimulator cells, DC Type 1, DC Type II, or autologous MO. On day 5 of culture, cells were pulsed for 18 hours with 0.5 uCi/well [methyl $^3$H] thymidine (specific activity 5 Ci/mmol, Amersham Life Science, Arlington Heights, Ill.). Cells were harvested onto filter paper (PhD Cell Harvester, Cambridge Technology, Inc., Waterford, Mass.) and specific activity was measured by liquid scintillation on the LKB 1218 Rackbeta liquid scintillation counter (Wallac, Inc., Finland). The results are summarized in FIG. 2. RESPONSE TO NAIVE (SOLUBLE) ANTIGEN: FIG. 3 schematically describes the naive antigen presentation experiment. Day 12 DC or autologous MO were pulsed for 24 hours with Keyhole limpet hemocyanin (KLH )—endotoxin free (Calbiochem, La Jolla, Calif.). Responding autologous T did not show any significant responding activity even when they were stimulated by dendritic cells. These data demonstrated that dendritic cells were the only cells truly capable of priming T cells with naive antigen, resulting in the subsequent antigen specific immune response. MORPHOLOGY: Cultured dendritic cells consisted mostly of large, non-adhered, veiled cells, with many exhibiting the characteristic dendritic branching processes.

Conclusions

From a single donor, we isolated large numbers of extremely pure peripheral blood monocytes. With cytokines, these monocytes were converted into Type I (baseline) or Type II (activated) dendritic cells exhibiting characteristic DC morphology, phenotype, and functional activity. These dendritic cells were capable of both stimulating allogeneic T cells in a mixed lymphocyte reaction and priming autologous T lymphocytes to a naive antigen. By this system, we generated large numbers (5–$10\times10^7$) of DC, sufficient for clinical therapeutic applications.

Example 2

TNF-α Induces a Reversible Proinflammatory State in Human Dendritic Cells

Dendritic cells (DCs) are fully functional antigen presenting cells reported to undergo irreversible "maturation" in response to TNF-α. In this example, we show the unexpected finding that the effects of TNF-α on human peripheral blood monocyte derived DCs are reversible and reinducible, and thus TNF-α does not induce terminal "maturation" of human DCs. Our data further demonstrates that TNF-α transiently activates DCs to a heightened proinflammatory state. These results show that dendritic cell phenotypes are more pleiotropic than earlier thought and suggest a central role for DCs not only in regulating the initiation, but also the duration and character of immune responses. Similar effects are observed upon incubation with IL-1α, IL-1β, or CD40 ligand; in certain applications, any of these cytokines, or a combination thereof, are equally preferred for making activated DCs. Slightly different phenotypes are observed when different cytokines are used for activation; for example, CD 40 ligand results in expression of IL-12 in activated DCs, while IL-1α, or IL-1, result in a more Th 1 like response.

The identification and characterization of DCs depend upon demonstration of identifiable morphologic characteristics, expression of a constellation of cell surface markers, and enhanced functional capacity. No single surface marker is widely accepted as identifying human DCs, although CD83 has been described as a marker for "mature" DCs (Zhou, et al. (1992) *J Immunol* 149:735). The lack of a lineage-specific marker has complicated the study of human DCs because the number of cells required to phenotypically evaluate cells recovered for functional experiments is often prohibitive. We were able to generate >$10^8$ human DCs from a single donor by culturing freshly purified monocytes with granulocyte macrophage colony stimulating factor (GM-CSF) and interleukin 4 (IL-4). Peripheral blood mononuclear cells (PBMC) were isolated from fresh normal donor apharesis packs by centrifugation over Ficoll (Pharmacia, Piscataway, N.J.) and were elutriated (counterflow centrifugation) (J6M, Beckman, Palo Alto, Calif.) yielding populations of monocytes and lymphocytes which were >95% pure as demonstrated by FACS analysis. A portion of the elutriated monocytes and the lymphocytes were cryopreserved in the vapor phase of liquid nitrogen for future use in functional testing and FACS analysis suspended in RPMI 1640 supplemented with 10% pooled human serum (BioWhittaker, Walkersville, Md.), L-glutamine (2 mM), sodium pyruvate (1 mM), non-essential amino acids (0.1 mM), penicillin (50 units/ml), streptomycin (50 ug/ml) (Gibco BRL Life Technologies, Gaithersburg, Md.), 7.5% DMSO (Fisher Chemical, Fair Lawn, N.J.). Monocytes were cultured at $1 \times 10^6$ cells/ml in RPMI 1640 (BioWhittaker, Walkersville, Md.) supplemented with L-glutamine (2 mM), sodium pyruvate (1 mM), non-essential amino acids (0.1 mM), penicillin (50 units/ml), streptomycin (50 ug/ml) (Gibco BRL Life Technologies, Gaithersburg, Md.), 2-mercaptoethanol (50 mM)(Sigma, St. Louis, Mo.) and 10% endotoxin free fetal calf serum (Atlanta Biologicals, Norcross, Ga.) at 37° C., 5% $CO_2$, GM-CSF (100 U/ml), and IL-4 (50 ng/ml, 100 U/ml) were added at day 0. TNF-α (20 ng/ml, 200 U/ml) was added to aliquots of DC cultures at 10–12 days, or as indicated, for 48 hours to obtain activated DCs. All cytokines were obtained through the Biological Resources Branch of the National Cancer Institute-Frederick Cancer Research and Development Center, Frederick, Md. Cultures were fed every 6–7 days by removing ½ of the culture volume and adding an equal volume of fresh media containing sufficient GM-CSF and IL-4 for the entire culture volume.

FIG. 5 provides the results of a FACS analysis of elutriated peripheral blood monocyte pool and autologous derived DCs. Cellular preparations were labeled with the designated antibodies and are represented by the shaded histograms. Solid lines represent negative control fluorochrome labeled antibody staining. Cells were incubated, after blocking in 5% human serum, for 15 min. at 4° C. in PBS, 2% bovine serum albumin & 0.1% sodium azide with FITC- or PE-conjugated mAb to CD3, CD4, CD8, CD11b, CD14, CD19, CD56, HLA DR, CD80, CD95 Ligand (Becton Dickinson, San Jose, Calif.), CD32, CD40, CD86, CD95, Pan MHC Class I (PharMingen, San Diego, Calif.), CD16 (20 ul of 1:100 3 G8, Medarex, Annandale, N.J.), CD11a, CD11c, CD33, CD34, CD54, CD83, CD154 (Coulter Immunotech Inc., Westbrook, Me.) and CD1a (clones: SFC119 Thy1A8 Coulter Immunotech Inc., Westbrook, Me.; OKT6, Ortho Diagnostic Systems Inc. Raritan, N.J.; M-T102 PharMingen, San Diego, Calif.; or NA1/34-HLK, Serotec, Washington, D.C.). CD1b, CD1c, and CD1a (clones B17.20.9, & BL6) (Coulter Immunotech Inc., Westbrook, Me.) were unconjugated and detected with FITC conjugated Fab'2 goat anti-mouse IgG incubated with 25 ml of a 1:20 dilution (Boehringer Mannheim Biochemicals, Indianapolis, Ind.). After washing, cells were resuspended in 1% parafornaldehyde and evaluated on a FACScan (Becton Dickinson, San Jose, Calif.) and analyzed using FlowJo software (Tree Star, San Carlos, Calif.). In addition to the histograms shown, staining in excess of 5% over control was not demonstrated for antibodies to CD2, CD3, CD19, CD56, and CD154.

The conversion to DCs was complete after 8 to 10 days and consistently resulted in a uniform population of DCs constituting a 15 to 25% yield, relative to the initial number of cells placed into culture (this yield was reproducible in over thirty separate normal donor preparations). The DCs were maintained in culture in excess of 28 days with no significant loss of cells while maintaining both their cell surface phenotype and functional capacity. Significant proliferation was not demonstrated as exemplified by background levels of 3H thymidine incorporation over this period.

For the purpose of this example, DCs generated from peripheral blood monocytes in the presence of GM-CSF and IL-4 are defined as "baseline DCs" and those exposed to TNF-α as "TNF-α activated DCs" (TNF-α DCs). The baseline DCs showed the typical morphology and expression of cell surface markers reported for "immature" DCs. Notably, these cellular preparations did not express monocyte (CD14), lymphocyte (CD3 & CD19), natural killer cell (CD56), myeloid precursor (CD34), and "mature" DC (CD83) markers. These DCs differed further from autologous monocytes in having elevated cell surface molecule expression of MHC class I and MHC class II antigens, CD80, and low but detectable CD1a. The interpretation of possible attenuated expression of CD11a, CD11b, and CD33 was complicated by the significantly higher intrinsic autofluorescence of DCs vs. autologous monocytes. Addition of TNF-α to the culture media resulted in an altered morphology and the induction, within 48 hours, of a shift in cell surface phenotype to that which has been reported for "mature" DCs (see, Background Of the Invention, above), including enhanced expression of CD40, CD54, CD80, and the induction of CD83 expression. Donor dependent changes including, variably attenuated expression of CD1a, CD11a, CD11b, CD32, and CD33, along with variable induction of CD86, were seen upon exposure to TNF-α, while the remainder of the panel of cell surface molecules (CD1b, CD1c, CD11c, CD16, and CD95) remained unchanged. The effects of TNF-α on cell surface phenotype was dose-dependent within the concentration range of 0.05 ng/ml to 20 ng/ml. Dendritic cells with this "mature" phenotype have been generated from CD34$^+$ progenitor cells (Galy et al. (1995) *Immunity* 3:459; Romani, et al. (1994) *J Exp Med* 180:83; Siena, et al. (1995) *Exp Hematol* 23:1463) in the presence of TNF-α. It is unlikely, however, that CD34$^+$ cells could account for generation of the "mature" DCs in our preparations since all monocyte and DC preparations demonstrated an absence of CD34$^+$ cells by flow cytometry and did not undergo proliferation.

Baseline and TNF-α activated DCs were evaluated for their immunostimulatory capacity in allogeneic mixed lymphocyte reactions (allo-MLRs) and for their ability to induce (prime) naive antigen responses. In allo-MLRs, both baseline and TNF-α activated DCs showed markedly enhanced stimulatory capacity relative to autologous monocytes and lymphocytes.

Figure 6:
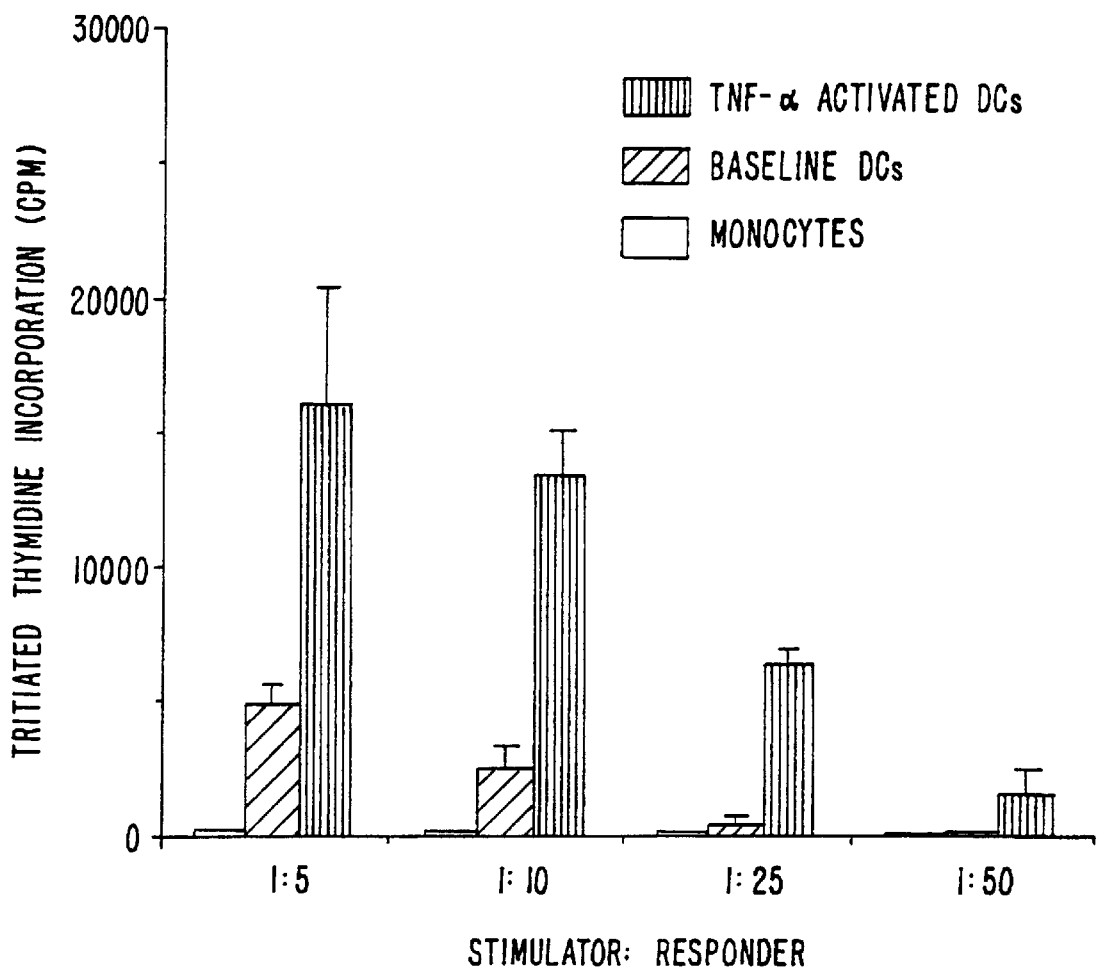
FIG. 6, is a graph showing titrated thymidine versus stimulator: responder.

TNF-α activated DCs were 2 to 3 times more potent as simulators than the baseline DCs. As shown in FIG. 6, autologous monocytes, dendritic cells and TNF-α activated DCs were compared for their ability to stimulate proliferative responses in allogeneic responding elutriated lymphocytes. Allogeneic responding T cells from normal donors were cultured at 1.0×10$^5$cells/well in 96 well flat-bottom microplates (Costar Corp., Cambridge, Mass.) with graduated numbers of irradiated (3000 rad from a 137Cs source) stimulator cells either, baseline DCs, TNF- activated DCs, or autologous monocytes. Cells were pulsed for 18 hours with 0.5 uCi/well [methyl 3H] thymidine (specific activity 5 Ci/mmol, Amersham Life Science, Arlington Heights, Ill.) on day 5 of culture. Cells were harvested using the Mach IIIm Harvester 96 (Tomtec Inc., Orange, Conn.) and specific activity was measured by liquid scintillation on the Micro-Beta Trilux liquid scintillation counter (Wallac, Inc., Finland).). Nearly identical results, both qualitative and quantitative, were obtained for 12 separate donor preparations. Results depicted are mean values for 5 replicate determinations per condition and error bars represent the respective standard deviation. The following controls had 3H thymidine incorporation, including +/−SD, <<1000 CPM at all dilutions and are therefore not depicted: responding lymphocytes alone and APCs alone (monocytes, baseline DCs, and TNF-α activated DCs).

Unprimed responding lymphocytes stimulated individually with each APC (monocytes, baseline DCs, and TNF-α activated DCs), and Non-restimulated primed responding lymphocytes primed individually with each APC (monocytes, baseline DCs, and TNF-α activated DCs). Dendritic cells are the only APC known to consistently prime naive antigen responses. The capacity for "immature" DCs to prime naive antigen responses has been controversial. Several groups have reported that only "mature" DCs are capable of initiating such an immune response (Romani et al. (1989) *J Exp Med* 169:1169; Reis e Sousa, et al. (1993) *J Exp Med* 178:509 (1993). Moll et al. (1993) *Eur J Immunol* 23:1595; Nijman, et al., (1995) *J Exp Med* 182:163; Rescigno, et al. (1997) *J Leuk Biol* 61:415. However, Caux and colleagues demonstrated the priming of naive antigen responses by both "mature" and "immature" DCs, defined on the basis of CD1a expression levels (Caux, et al. (1992) *Nature* 360:258; Caux, et al. (1995) *J Immunol* 155:5427).

Figure 7:
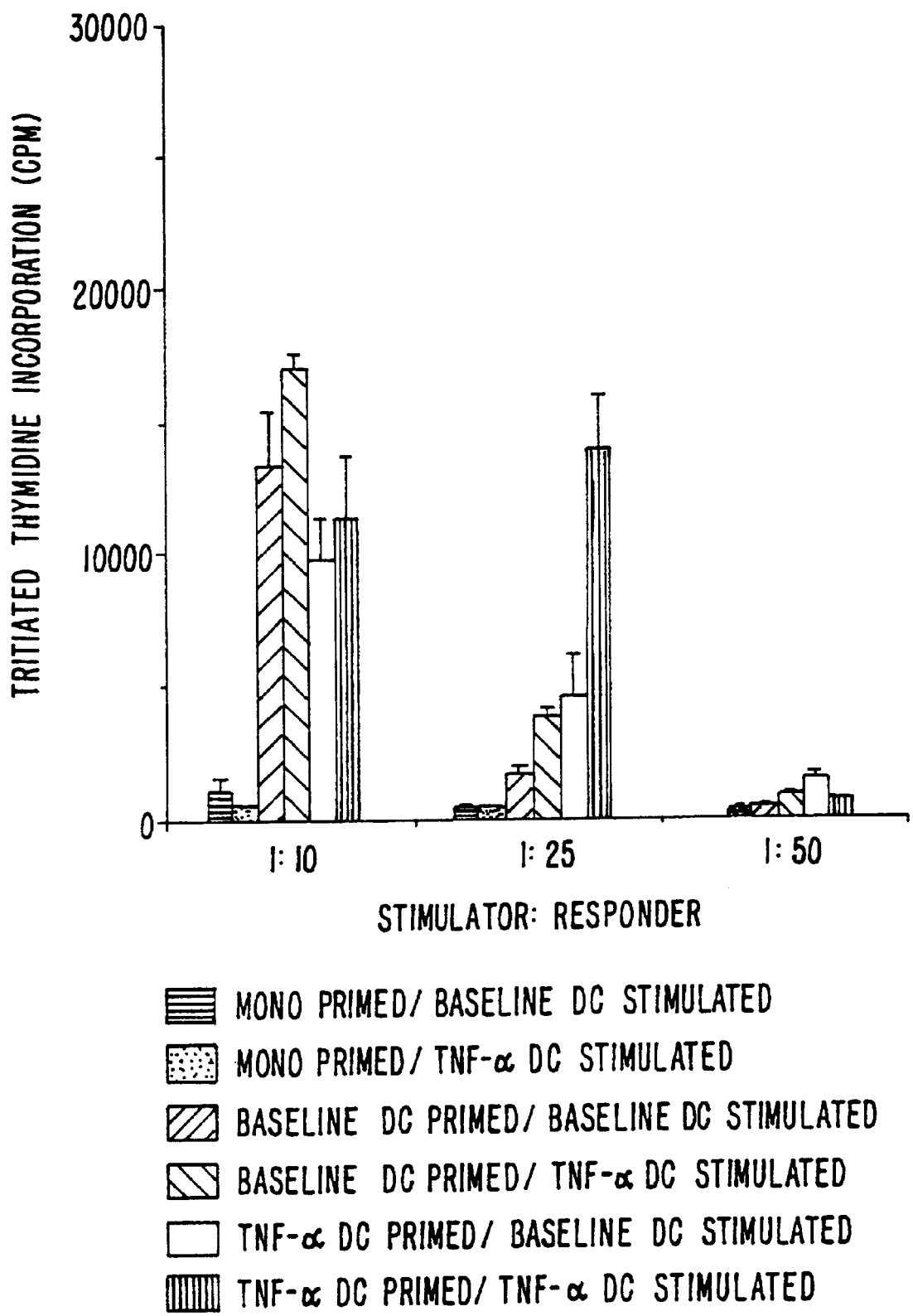
FIG. 7 is a graph showing titrated thymidine versus stimulator:responder for 6 separate experiments.

We evaluated our DC preparations for the capacity to prime an autologous, naive antigen immune response using endotoxin free KLH (Calbiochem, San Diego, Calif.) as the naive antigen (Gebel et al. (1983) *J Immunol* 130:29; Mehta-Damani, et al. *Eur J Immunol* 25:1206). As shown in FIG. 7, autologous lymphocytes were initially primed with antigen pulsed APCs, allowed to become quiescent over 10 days, then restimulated with antigen pulsed APCs for five days prior to evaluation for proliferation by tritiated thymidine incorporation.

All cultures for the evaluation of naive antigen immune responses were performed in AIM V media supplemented with L-glutamine (2 mM), sodium pyruvate (1 mM), non-essential amino acids (0.1 mM), penicillin (50 units/ml), streptomycin (50 ug/ml)(Gibco BRL Life Technologies, Gaithersburg, Md.), and 2-mercaptoethanol (50 mM) (Sigma, St. Louis, Mo.). APCs, either Day 12 dendritic cells or autologous monocytes, were incubated for 18–24 hours with "endotoxin free" keyhole limpet hemocyanin (KLH) (Calbiochem, La Jolla, Calif.) at a concentration of 10 μg/ml; the resulting endotoxin level of this lot was less than 0.04 EU (endotoxin unit) per mililiter. Activated DCs were exposed to TNF-α for 48 hours prior to their addition to responding lymphocytes. All APCs were washed×3 with PBS before addition to responding cells. Responding autologous lymphocytes were mixed with graduated numbers of KLH pulsed, washed, stimulator dendritic cells or monocytes. Cells were cultured together for 10 days. These "primed" T cells @1×105 cells/well were then restimulated with a second set of KLH pulsed, washed, irradiated, autologous APCs (either dendritic cells or monocytes) and cultured together for 5 days. After 5 days of culture, cells were pulsed for 18 hours with 3H thymidine, harvested, and measured as described (Zhou et al (1992), supra). Baseline DCs and TNF-α activated DCs were cultured as described (). This data is from one of three experiments each of which used different donor preparations and all three experiments yielded similar results. The following controls had 3H thymidine incorporation, including +/−SD, <<2000 CPM at all dilutions and are therefore not depicted: Unprimed responding lymphocytes, Priming APCs (monocytes, baseline DCs, and TNF-α activated DCs), stimulating APCs (monocytes, baseline DCs, and TNF-α activated DCs).

Both the baseline and TNF-α activated DCs primed naive antigen immune responses, while autologous monocytes had no such ability. Thus, both of the DC preparations, baseline and TNF-α activated DCs, have the combination of morphologic, phenotypic, and functional characteristics currently used to define human DCs.

If the effect of TNF-α on immature DCs represents a "maturation" event, then the phenotypic and functional alterations should not be reversible. To test the hypothesis that TNF-α reversibly activates DCs we performed 'wash out' experiments evaluating cell surface molecule expression (FIG. 8) and functional capacity in allo-MLRs (FIG. 9).

Figure 8D:
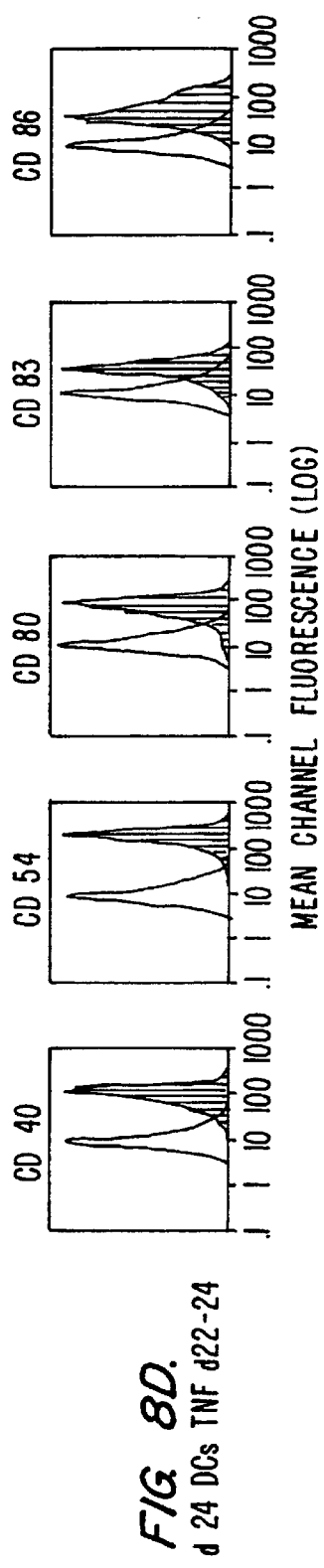
Figure 8E:
Figure 8F:
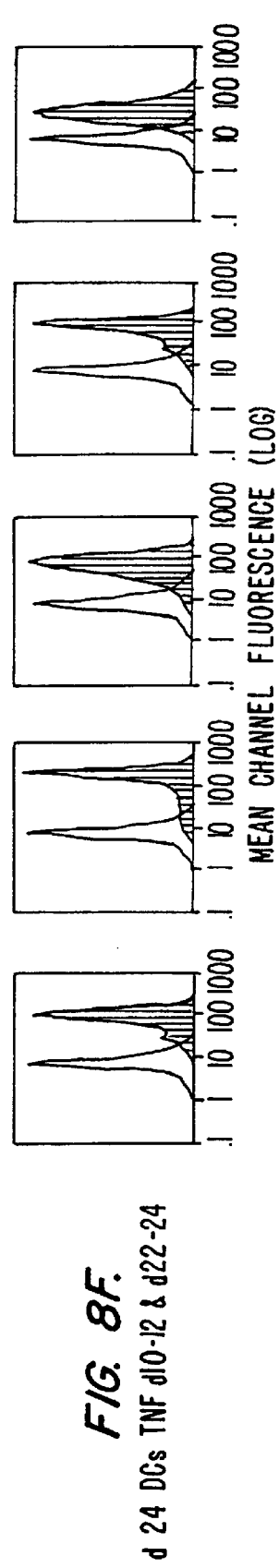

FIG. 8 shows a reversible cell surface marker phenotype induced by TNF-α and evaluated by FACS analysis. Single donor, autologous cellular preparations were labeled with selected antibodies as described above and are represented by the shaded histograms. Solid lines represent negative control fluorochrome labeled antibody staining. Row A=12 day baseline DCs cultured. Row B=TNF-α activated DCs, identical in age to A. Row C=24 day baseline DCs. Row D=24. day TNF-α activated DCs, activated with TNF-α for the final 48 hours of the experiment. Row E=24 day DCs activated with TNF-α for 48 hours at day 10, cultured in the absence of TNF-α for the remainder of the experiment. Row F=24 day DCs activated with TNF-α for 48 hours at day 10, cultured in the absence of TNF-α for 10 days, and restimulated with TNF-α for the final 48 hours of the experiment. These data are representative of four independent experiments. Single donor DCs were divided at day 10 with one part of the preparation exposed to TNF-α for 48 hours. A portion of each of the resulting twelve day old preparations were analyzed. Both demonstrated the expected cell surface phenotype and enhanced functional capacity relative to each other and to autologous monocytes. The remaining portions of these baseline and TNF-α activated DC cultures were then washed twice with PBS and placed into standard DC culture media without TNF-α. After 7 or 10 days there was no discernible difference in either the cell surface molecule expression or the allo-MLR stimulatory capacity between the formerly activated DCs and autologous DCs maintained in the absence of TNF-α for this same period.

Figure 9:
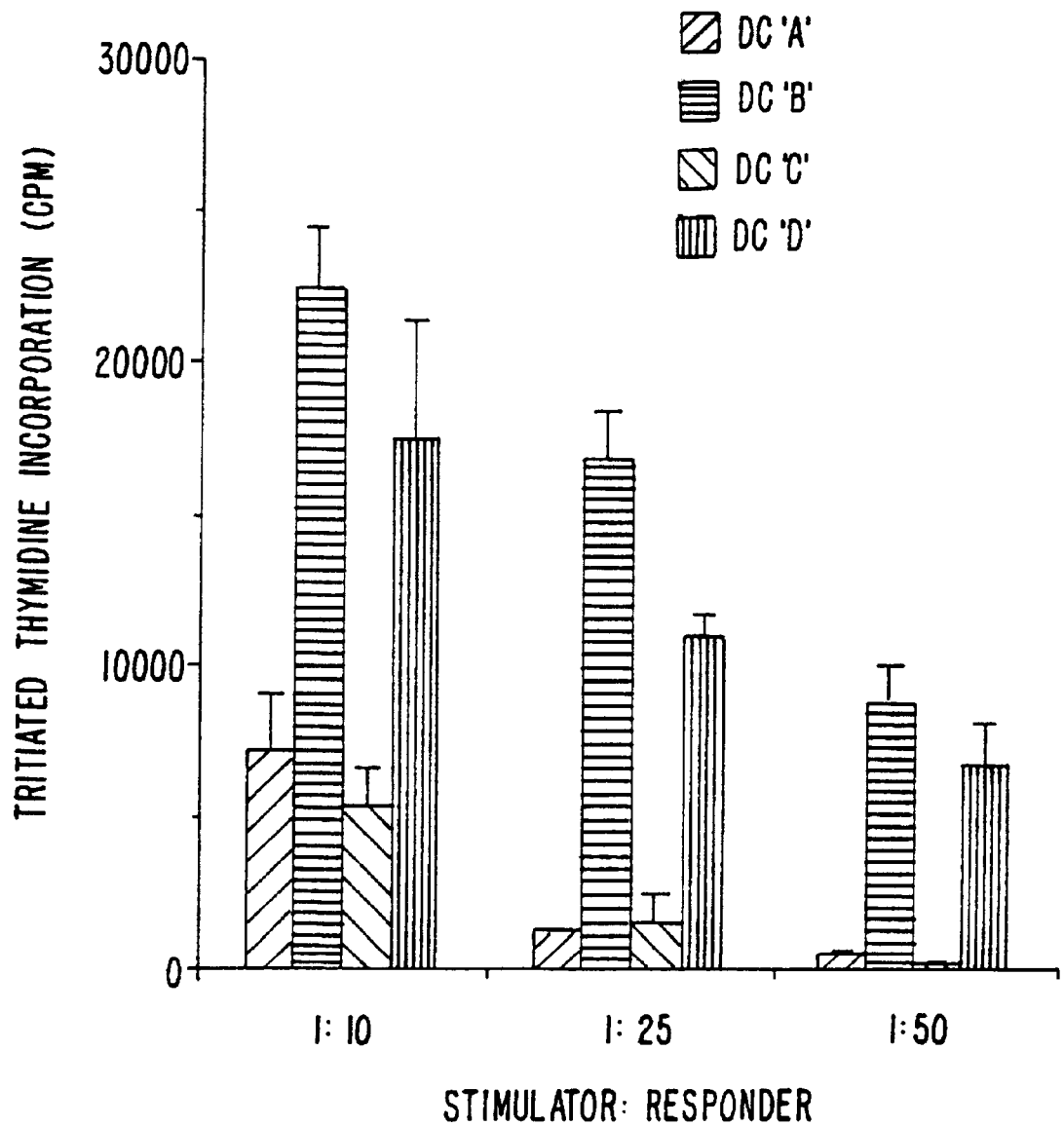
FIG. 9 is a graph showing titrated thymadine incorporation versus stimulator:responder for DC 'A' through DC 'D.'

FIG. 9 shows a reversible induction by TNF-α of enhanced DC stimulatory function in allogeneic mixed lymphocyte reactions. DCs were compared for their ability to stimulate proliferative responses in allogeneic responding elutriated lymphocytes as described above. Depicted dendritic cell preparations are 24 day cultures as listed: DC 'A' represent baseline DCs maintained for the duration of the experiment, DC 'B' represent TNF-α activated DCs, activated with TNF-α for the final 48 hours of the experiment, "DC 'C' represent DCs initially activated with TNF-α for 48 hours at day 10 and cultured in the absence of TNF-α for the remainder of the experiment, and DC 'D' represent DCs initially activated with TNF-α for 48 hours at day 10, cultured in the absence of TNF-α for 10 days, and then restimulated with TNF-α for the final 48 hours of the experiment. Allo-MLRs performed with a portion of these cultures at day 12, with the first exposure to TNF-α, gave results nearly identical to DC 'A' and DC 'B'. The error bars represent standard deviation of the mean for five replicate wells. All responding allogeneic lymphocytes were isolated from the same donor. The following controls had 3H thymidine incorporation, including +/−SD, <<1000 CPM at all dilutions and are therefore not depicted: responding lymphocytes alone and APCs alone (monocytes, baseline DCs, and TNF-α activated DCs). This data is representative of three separate 'wash out' experiments all of which yielded similar results. Cell surface phenotype for these preparations are represented in FIG. 8 by rows C, D, E, and F, respectively.

Re-exposure of the formerly activated DCs to TNF-α for 48 hours again elicited the same activated cell surface phenotype (FIG. 8) and the enhanced immunostimulatory function (FIG. 9). These phenotypic shifts were comparable to those seen in the control 19 day old DCs, maintained in GM-CSF and IL-4 over the entire "wash out" period, and exposed for the first time to TNF-α for 48 hours. Thus, these effects of TNF-α are reversible and re-inducible, thereby arguing strongly for activation vs. maturation.

To further characterize this TNF-α induced activation, we investigated the expression of chemokines and cytokines in baseline and TNF-α activated DCs using ribonuclease protection assays (RPA). The mRNA levels for the chemokine RANTES and the cytokines IL-15, IL-12 p40, TNF-α, LT-α, LT-β were all induced, two to thirty fold, upon TNF-α exposure while IL-10, TGF-β1, TGF-β2, IL-1 RA, MIP-1β, and MCP-1 mRNA levels were attenuated to levels 50 to 20% of 'baseline'. Other cytokine and chemokine mRNA levels were not significantly affected with activation by TNF-α.

Identical "wash out" experiments, described above, were performed to evaluate the reversibility of TNF-α induced modulation of the cytokine/chemokine expression patterns. The results demonstrated a reversible and re-inducible modulation of cytokine/chemokine expression that was entirely concordant with the functional and cell surface phenotypic changes. The TNF-α induced cytokines and chemokines are characteristic proinflammatory immune mediators and the attenuated mRNAs are generally representative of counter regulatory or immune suppressive cytokines (Van der Meide and Schellekens (1996) *Biotherapy* 8:243; Rollins (1997) *Blood* 90:909). This pattern of modulation of cytokine and chemokine expression suggests that the accentuated immunostimulatory capacity seen with TNF-α activated DCs is due to both induction of proinflammatory mediators and cell surface accessory/costimulatory molecules.

The entire range of phenotypic shifts induced by TNF-α in human peripheral blood monocyte derived DCs were reversible and re-inducible. The use of large single donor preparations for these "washout" experiments and the absence of two distinct populations of "immature" and "mature" DCs by cell surface markers during the 'washout' of TNF-α support a true reversion of phenotype and not death of "mature" DCs with replenishment from a pool of "immature" DCs upon re-exposure to TNF-α. The somewhat prolonged period required for reversion of the activated phenotype is consonant with the limited proliferative capacity of these cells and their ability to be maintained in culture for at least a month without attenuation of any defining properties.

The paracrine induction of TNF-α message likely plays a role in the slow return to a baseline state in these DCs. Previous reports of irreversible TNF-α induced "maturation" in human DCs were based on no change in phenotype in "several days" (Sallusto et al. (1995) *J Exp Med* 182:389) or at "3 days" (Bender et al. (1996) *J Immunol Methods* 196:121). Notably, after five days of the wash out period we observed only partial reversion of the cell surface phenotype. Therefore, the apparent conflicting observations and interpretation of effects of TNF-α on human DCs may be the result of differences in experimental design.

It has been postulated that "immature" DCs reside in the periphery, sampling their environment, but require "maturation" to initiate an immune response. Our data suggest that baseline DCs are capable of initiating and regulating immune responses, including naive antigen responses, albeit with 2 to 3 fold lower efficiency than TNF-α activated DCs. These baseline DCs have the typical morphology of "immature" DCs, do not express CD83, and when exposed to TNF-α modulate their cell surface phenotype and functional capacity in a manner described by others as being associated with "maturation." Additionally, our baseline DCs are significantly more active in the process of macropinocytosis than TNF-α activated DCs. Therefore, it is unlikely that these baseline DCs represent partially matured DCs. During the process of "maturation" it has been suggested that DCs induce MHC synthesis and expression, cease sampling the environment via macropinocytosis, migrate to regional lymphoid tissues with their existing antigen repertoire, and initiate an immune response (Cumberbatch and Kimber (1995) *Immunology* 84:31; Wan, et al. (1996) *Immunology* 88:284; McWilliam, et al., (1996) *J Exp Med* 184:2429; Cumberbatch et al. (1997) *Immunology* 92:388; Cella et al. (1997) *Nature* 388:782. While our results demonstrated a transient TNF-α effect, they do not contradict this general hypothesis. Moreover, characterization of the cytokine and chemokine message levels would suggest that activation of DCs by TNF-α results not only in induction of proinflammatory mediators, but also in the disengagement of a "physiologic brake" on the immune response. Relatively little attention has been paid to the role of DCs in the autoregulation of acute immune responses. However, the cytokines and chemokines expressed by human monocyte derived DCs suggests that they not only initiate, but also have the capacity to regulate both the amplitude, duration, and character of the immune response. This capacity is further supported by our observation that lymphocytes primed with baseline DCs had more of a Th2 bias than lymphocytes primed with TNF-α activated DCs.

The effect of TNF-α in modifying DCs into critical initiators and regulators of immune/inflammatory responses suggests that interplay between them would be relevant for appropriately regulated immune responses. TNF-α is a pleiotropic cytokine that acts as a pivotal immune mediator in a wide range of immunologic and inflammatory conditions (Vassalli (1992) *Ann Rev Immunol* 10:41 1; Pasparakis et al. (1996) *Cytokine Growth Factor Rev* 7:223). The role of TNF-α in the initiation of defensive inflammatory responses and in the simultaneous initiation of counter regulatory or immune suppressive responses, is exemplified by the profound physiologic disturbances when TNF-α expression is persistent and/or dysregulated, i.e. septic shock and autoimmune states. The persistence of a TNF-α activated DC phenotype with its enhanced immunostimulatory capacity could lead to dysregulation of the immune response. Therefore, the gradual reversion to a "baseline" status that includes re-induction of counter-regulatory immune mediators (such as the TGF-βs and IL-10), which we demonstrated in vitro, is relevant to appropriate regulation of the immune response.

A role of TNF-α and related family members in the appropriate immunologic function of DCs and Langerhan's cells is supported by the findings of absent or disorganized lymph nodes & Peyer's patches with absent follicular dendritic cells in TNF-α/lymphotoxin knock out mice and similar lymphoid tissue histology in TNF receptor knock out mice. The role of TNF-α in human DC differentiation and "maturation" can now be re-evaluated in light of our data demonstrating transient and reversible modulations of DC phenotype as well as the observation that TNF-α induces expression of the GM-CSF receptor on $CD34^+$ bone marrow progenitor cells. In contrast to murine systems, where GM-CSF is sufficient to generate bone marrow derived DCs, the generation of human DCs from $CD34^+$ bone marrow progenitor cells requires additional cytokines, such as TNF-α. Thus, the recent reports characterizing $CD34^+$ derived DCs as 2-3× more potent than peripheral blood derived (baseline) DCs may represent the difference between evaluating TNF-α activated DCs and baseline DCs. The ability of other cytokine combinations to substitute for TNF-α in the generation of DCs from CD34+ progenitors suggests that other immune mediators will also induce modulation and/or activation of DC phenotype and function. The capacity of DCs to respond to various immune mediators is not unexpected given the requisite flexibility of the system and the central role of DCs in the initiation and regulation of immune responses. The ultimate fate of these activated DCs will likely depend upon other immune mediators and may range from apoptosis (with continuous activating stimuli) to quiescent or "memory" states, or even return to the periphery with resumption of antigenic surveillance.

Example 3

Pre Vaccine Patient: Autologous in Vitro and Anti-idiotypic Immunoglobulin Proliferative Immune Response In this example, we show the potent capacity of DCs derived from a cancer patient to elicit an ex-vivo immune response to their own tumor antigen (in this case, idiotypic immunoglobulin from a B cell non-Hodgkin's lymphoma patient). The system was entirely autologous.

As above, all cultures for the evaluation of antigen immune responses were performed in AIM V media supplemented with L-glutamine (2 mM), sodium pyruvate (1 mM), non-essential amino acids (0.1 mM), penicillin (50 units/ml), streptomycin (50 ug/ml) (Gibco BRL Life Technologies, Gaithersburg, Md.), and 2-mercaptoethanol (50 mM)(Sigma, St. Louis, Mo.). APCs, either Day 12 dendritic cells or autologous monocytes, were incubated for 18–24 hours with idiotypic immunoglobulin from a B cell non-Hodgkin's lymphoma patient, derived by limiting dilution cloning. Immunoglobulin was present at a concentration of 100 µg/ml.

Baseline DCs were exposed to TNF-α for 48 hours prior to their addition to responding lymphocytes. All APCs were washed×3 with PBS before addition to responding cells. Responding autologous lymphocytes were mixed with graduated numbers of pulsed, washed, stimulator dendritic cells or monocytes. Cells were cultured together for 10 days. These "primed" T cells @$1\times10^5$ cells/well were then restimulated with a second set of pulsed, washed, irradiated, autologous APCs (either dendritic cells or monocytes) and cultured together for 5 days. After 5 days of culture, cells were pulsed for 18 hours with 3H thymidine, harvested, and measured by standard methods. (Zhou et al (1992), supra).

Figure 10:
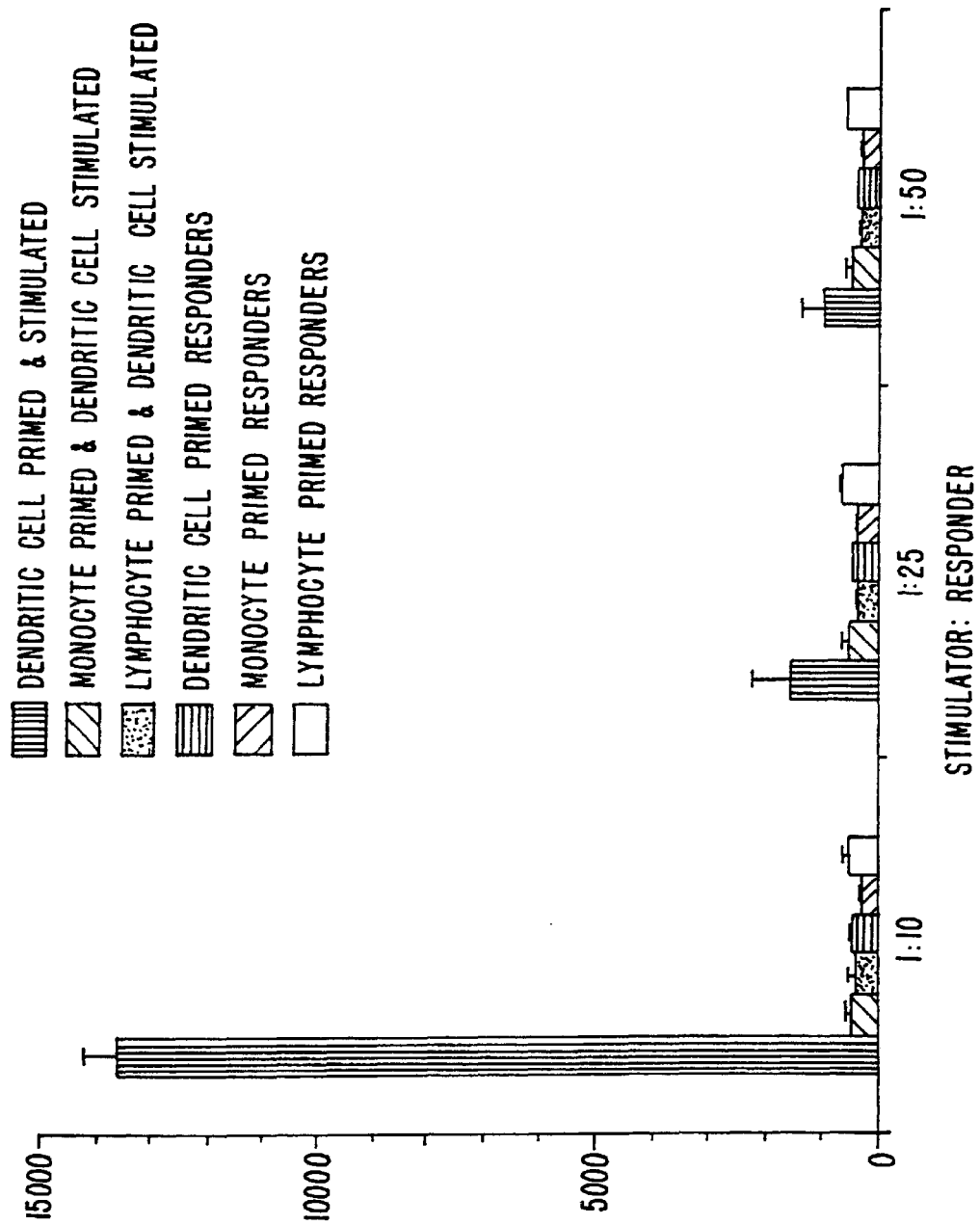
FIG. 10 is a graph showing the results of a pre-vaccine patient: autologous in vitro anti-idiotypic immunoglobulin proliferative immune response.

The results are illustrated in FIG. 10. Of note, the best response was generated with both primary and secondary stimulation using DCs at a fairly high (1:10) stimulator to responder ratio. This clearly shows the advantage of ability to generate large numbers of autologous DCs as detailed above.

Using these methods, ex vivo vaccination can be employed. In one ex vivo embodiment, autologous DCs and purified lymphocytes are generated and tumor associated antigen expressing DCs are used to generate proliferating and activated antigen specific lymphocytes that are expanded and administered, adoptively, back into the patient. This is performed, e.g., in the setting of bone-marrow transplantation where cells from an allogeneic donor are generated without exposing the donor to the risks of an "anti-tumor vaccination." As noted above, the DCs are manipulable to drive a particular type of response (e.g., Th1 or Th2).

In addition to ex vivo methods, in vivo therapy can also be performed. This relies on administering tumor antigen expressing DCs directly to the patient, alone, or in combination with any other approach noted above. Appropriately manipulated DCs can act in an immunosuppressive or immunotolerant role.

All publications and patent applications cited in this specification are herein incorporated by reference as if each individual publication or patent application were specifically and individually indicated to be incorporated by reference in its entirety for all purposes. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of expanding a population of monocytes from peripheral blood and differentiating the expanded population into dendritic cells, comprising:

first incubating the monocytes in the presence of IL-3 and under conditions which do not differentiate the monocytes into dendritic cells; thereby expanding the population of the monocytes; and subsequently incubating the expanded population with GM-CSF and IL-4, thereby differentiating the expanded population of monocytes into dendritic cells.

2. The method of claim 1, wherein the IL-3 is present at a concentration of between 5 and about 50 ng/ml.

3. The method of claim 1, further comprising incubating the dendritic cells with TNF-α, thereby generating activated dendritic cells.

4. The method of claim 1, further comprising incubating the dendritic cells with TNF-α, thereby transiently activating the dendritic cells to a proinflammatory state.

5. The method of claim 1, further comprising leukapheresis of peripheral blood mononuclear cells from a patient, thereby providing isolated peripheral blood, followed by elutriation of the isolated peripheral olood to provide isolated monocytes, which isolated monocytes are incubated in the presence of IL-3.

6. The method of claim 1, further comprising isolating monocytes from a patient, which isolated monocytes are incubated in the presence of IL-3 to provide said expanded population of monocytes.

7. The method of claim 1, further comprising isolating monocytes from a patient, which isolated monocytes are incubated in the presence of IL-3 to provide said expanded population of monocytes, the method further comprising presenting a peptide on the surface of the dendritic cells.

8. The method of claim 1, further comprising isolating monocytes from a patient, which isolated monocytes are incubated in the presence of IL-3 to provide said expanded population of monocytes, further comprising:

presenting a peptide on the surface of the dendritic cells, thereby providing a population of antigen presenting dendritic cells; and, activating a population of T cells with the population of antigen presenting dendritic cells, thereby providing an activated population of T cells.

9. The method of claim 8, wherein the step of activating the population of T cells occurs in vitro.

10. The method of claim 8, further comprising exposing the antigen presenting dendritic cells to TNF-α.

11. The method of claim 8, wherein the step of activating the population of T cells occurs in vivo.

12. The method of claim 8, the method further comprising introducing said activated T cells into the patient.

13. The method of claim 8, the method further comprising introducing said antigen presenting dendritic cells into said patient.

14. The method of claim 13, wherein the dendritic cells stimulate NK cell activity in the patient.

15. The method of claim 8, wherein the antigen is derived from a protein or carbohydrate expressed on the surface of a transformed cell.

16. The method of claim 8, wherein the peptide is derived from a protein selected from the group consisting of HIV Gag, HIV Env, c-erb-β-2/HER2/neu, PEM/MUC-1, Int-2, Hst, BRCA-1, BRCA-2, truncated EGFRvIII, MUC-1, p53, ras, RK, Myc, Myb, OB-1, OB-2, BCR/ABL, GIP, GSP, RET, ROS, FIS, SRC, TRC, WTI, DCC, NF1, FAP, MEN-1, ERB-B1 MART-1, gp-100, PSA, HBVc, HBVs, HPV E6, HPV E7, an idiotypic immunoglobulin, tyrosinase, MAGE-1, trp-1, and a mycobacterial antigen.

17. The method of claim 8, wherein the peptide has a carbohydrate epitope.

18. The method of claim 1, further comprising contacting said dendritic cell with a protein differentially expressed on a cell selected from the group consisting of: a cancer cell, a bacterial cell, a parasitically infected cell and a virally infected cell.

19. The method of claim 18, wherein the protein is expressed on the surface of a transformed cell.

20. The method of claim 18, wherein the differentially expressed protein is selected from the group consisting of HIV Gag, HIV Env, HER-2, MART-1, gp-100, PSA, HBVc, HBVs, tyrosinase, MAGE-1, trp-1, mycobacterial antigens, and CEA.

21. The method of claim 1, further comprising transducing said dendritic cell with a nucleic acid vector which encodes a protein differentially expressed on a cell selected from the group consisting of: a cancer cell, a bacterial cell, a parasitically infected cell and a virally infected cell.

22. A method of activating a T cell, comprising:

expanding a population of monocytes from peripheral blood and differentiating the expanded population into dendritic cells according to the method of claim 1; and, contacting the T cell with at least one of said dendritic cells;

thereby producing an activated T-cell.

23. The method of claim 22, wherein the dendritic cell contacts the T cell in vitro.

24. The method of claim 22, wherein the T cell is a helper T cell.

25. The method of claim 22, wherein the dendritic cell presents an antigenic protein comprising a peptide subsequence derived from a peptide expressed on the surface of a cancer cell.

26. The method of claim 25, wherein the activated T cell is competent to kill the cancer cell.

27. The method of claim 25, wherein the activated T cell mediates a helper T cell response.

28. The method of claim 25, wherein the antigen is derived from a protein or carbohydrate expressed on the surface of a transformed cell.

29. The method of claim 25, wherein the activated T cell recognizes an antigen derived from a protein selected from the group consisting of HIV-1 Gag, HIV-1 Env, HER-2, MART-1, gp-100, PSA, HBVc, HBVs, tyrosinase, MAGE-1, trp-1, a mycobacterial antigen, and CEA.

30. A method for detecting the ability of an antigenic protein or peptide to induce T cell mediated anti-cancer cell activity, comprising:

expanding a population of monocytes from peripheral blood and differentiating the expanded population into dendritic cells according to the method of claim 1;

loading the antigenic protein or peptide onto the dendritic cells;

contacting a T-cell with at least one of the loaded dendritic cells, thereby providing an activated T cell;

contacting a cancer cell with the activated T cell; and, monitoring the effect of the activated T cell on the cancer cell;

thereby detecting the anti-cancer cell activity of the T cell activated by contact with the dendritic cell comprising the antigenic protein or peptide.

31. The method of claim 30, wherein the antigenic peptide is derived from HER-2, and the cancer cell is a breast cancer cell.

32. The method of claim 30, wherein the antigenic peptide is derived from a protein selected from the group consisting of MART-1 and gp-100, wherein the cancer cell is a melanoma cell.

33. The method of claim 30, wherein the antigenic peptide is derived from CEA and the cancer cell is a colon cancer cell.

34. The method of claim 30, wherein the T cell is contacted with the dendritic cell in vivo.

35. The method of claim 30, wherein the T cell is contacted with the dendritic cell in vitro.

36. The method of claim 30, wherein the T cell is contacted with the dendritic cell in vitro and contacted with the cancer cell in vitro.

37. The method of claim 30, wherein the T cell is contacted with the dendritic cell in vivo and contacted with the cancer cell in vivo.

38. A method of killing a target cell, comprising:
   expanding a population of monocytes from peripheral blood and differentiating the expanded population into dendritic cells according to the method of claim 1;
   loading the dendritic cells with an antigenic protein or peptide fragment of the target cell;
   contacting the T-cell with at least one of the loaded dendritic cells to activate the T-cell by; and
   contacting the target cell with the activated T cell.

39. The method of claim 38, wherein the target cell is contacted by the activated T cell in vivo.

40. The method of claim 38, wherein the target cell is contacted by the activated T cell in vitro.

41. The method of claim 38, wherein the target cell is selected from the group consisting of a cancer cell, an intracellularly infected with a bacterial cell, and, a virally-infected cell.

42. A method of making a pharmaceutical composition comprising a pharmaceutically acceptable carrier and a population of at least about $10^6$ antigen-loaded dendritic cells; said method comprising:
   expanding a population of monocytes from peripheral blood and differentiating the expanded population into dendritic cells according to the method of claim 1; and
   loading a heterologous protein or peptide onto the dendritic cells to make the antigen-loaded dendritic cells; wherein the loaded dendritic cells are competent to activate T-cells to kill a target cell in vitro; and
   formulating the antigen loaded dendritic cells in a pharmaceutically acceptable carrier.

43. The method of claim 42, wherein the dendritic cells are made from an expanded population of monocytes by incubating the population with IL-4 and GM-CSF and with one or more additional ligands selected from IL-1α, IL-1β and Cd40 ligand.

44. The method of claim 42, wherein the dendritic cells are primarily activated dendritic cells.

45. The method of claim 42, wherein the population of dendritic cells is competent to activate said T cells against said target cell in vivo.

46. The method of claim 42, wherein the heterologous protein is selected from the group of proteins consisting of HER-2, MART-1, gp-100, PSA, HBVc, HBVs, tyrosinase, MAGE-1, trp-1 and CEA.

47. The method of claim 42, wherein formulating the antigen loaded dendritic cells in a pharmaceutically acceptable carrier further comprises formulating the antigen loaded dendritic cells with a T cell in a pharmaceutically acceptable carrier.

48. The method of claim 42, wherein the target cell is a cancer cell.

49. The method of claim 1, wherein said monocytes are $CD14^+$ monocytes.

50. The method of claim 30, wherein said monocytes are $CD14^+$ monocytes.

51. The method of claim 30, wherein said monocytes are $CD14^+$ monocytes.

52. The method of claim 38, wherein said monocytes are $CD14^+$ monocytes.

53. The method of claim 42, wherein said monocytes are $CD14^+$ monocytes.

* * * * *

UNITED STATES PATENT AND TRADEMARK OFFICE
CERTIFICATE OF CORRECTION

PATENT NO.    : 6,479,286 B1                      Page 1 of 1
DATED         : November 12, 2002
INVENTOR(S)   : Edward L. Nelson et al.

It is certified that error appears in the above-identified patent and that said Letters Patent is hereby corrected as shown below:

<u>Title page,</u>
Item [22], should read:

-- [22] PCT Filed:     May 20, 1998 --

Signed and Sealed this

First Day of July, 2003

JAMES E. ROGAN
*Director of the United States Patent and Trademark Office*